United States Patent [19]

Preiss et al.

[11] 4,215,118
[45] Jul. 29, 1980

[54] 2-HETERO-ACETAMIDO-PENICILLANATES AND CEPHALOSPORINATES

[75] Inventors: Michael Preiss; Hans-bodo König; Karl G. Metzger, all of Wuppertal; Peter Feyen, Mettmann, all of Fed. Rep. of Germany

[73] Assignee: Bayer Aktiengesellschaft, Leverkusen, Fed. Rep. of Germany

[21] Appl. No.: 923,518

[22] Filed: Jul. 10, 1978

[30] Foreign Application Priority Data

Jul. 16, 1977 [DE] Fed. Rep. of Germany ....... 2732283

[51] Int. Cl.² ............... A61K 31/535; C07D 499/44
[52] U.S. Cl. ........................ 424/248.4; 260/239.1; 424/248.5; 424/248.51; 424/250; 424/256; 424/263; 424/267; 424/269; 424/270; 424/271; 542/420
[58] Field of Search ............ 542/420; 260/239.1; 424/271, 248.4, 248.5, 248.51, 250, 256, 263, 269, 267, 270

[56] References Cited

U.S. PATENT DOCUMENTS

| 3,959,258 | 5/1976 | König et al. | 260/239.1 |
| 3,974,142 | 8/1976 | König et al. | 260/239.1 |
| 4,087,424 | 5/1978 | Saikawa et al. | 260/239.1 |

Primary Examiner—Norman Morgenstern
Assistant Examiner—Vera C. Clarke
Attorney, Agent, or Firm—Sprung, Felfe, Horn, Lynch & Kramer

[57] ABSTRACT

2-Hetero-acetamido-penicillanates and cephalosporinates of the formula

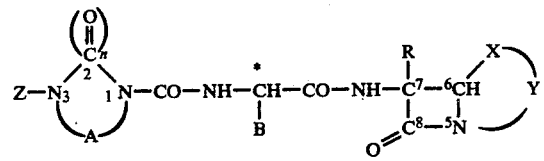

in which
R is hydrogen or lower alkoxy,
Z is

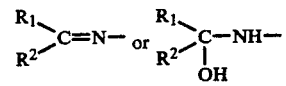

$R^1$ and $R^2$ independently or together are various radicals,
A is $-CH_2-CH_2-$, $-CH_2-CH_2-CH_2-$ or

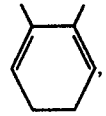

n is 1 or 2,
X is S,O,SO,SO₂ or —CH₂—,
Y is the balance of a penicillin or cephalosporin moiety, and
B is a heterocyclic radical, in the form of the acid, a hydrate thereof, a salt thereof or a salt of the hydrate, exhibit marked anti-bacterial properties rendering them suited for use as antibiotics and animal feed supplements.

18 Claims, No Drawings

2-HETERO-ACETAMIDO-PENICILLANATES AND CEPHALOSPORINATES

The present invention relates to new β-lactam compounds, processes for their preparation and their use as medicaments, in particular as antimicrobial agents and as agents for promoting growth and for improving feedstuff utilization in animals.

It has already been disclosed that certain α-(imidazolidin-2-oxo-1-yl-carbonylamino)-benzylpenicillins are antibacterially active (compare Belgian Patent Specification No. 767,647 and 767,648 and DT-OS (German Published Specification) No. 2,152,968).

The new β-lactam antibiotics according to the invention differ chemically from the known compounds of the state of the art by, above all, the heterocyclic ring in the α-position in the acyl side-chain.

The invention relates to new β-lactam compounds of the formula (I)

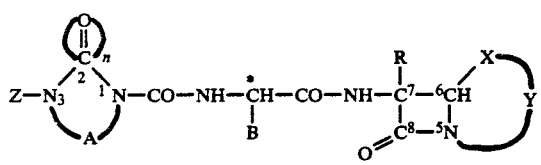

pharmaceutically usable salts thereof, or hydrates thereof in which

R denotes hydrogen or lower alkoxy,

Z denotes a group

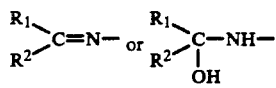

in which $R^1$ and $R^2$ are identical or different and denote hydrogen, optionally substituted alkyl or alkenyl, optionally substituted cycloalkyl, cycloalkenyl or cycloalkadienyl, optionally substituted aralkyl, optionally substituted aryl, optionally substituted heterocyclyl, carboxyl, methoxycarbonyl, ethoxycarbonyl, cyano, nitro, lower alkylcarbonyl, —CONH$_2$, —CONHCH$_3$, —CON(CH$_3$)$_2$, —SO$_2$NH$_2$, —SO$_2$—NHCH$_3$ or —SO$_2$N(CH$_3$)$_2$ and $R^1$ and $R^2$, together with the carbon atom to which they are bonded, can form a 3-membered to 7-membered saturated or unsaturated carbocyclic or heterocyclic ring, which can be substituted;

A denotes —CH$_2$—CH$_2$—, —CH$_2$—CH$_2$—CH$_2$— or

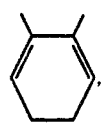

n is 1 or 2,

B denotes a saturated or unsaturated optionally substituted heterocyclic ring,

X denotes S, O, SO, SO$_2$ or —CH$_2$—, and

Y denotes a group

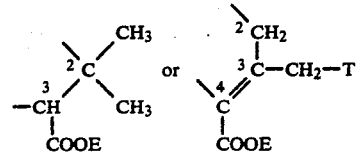

in which the carbon atom which carries the group —COOE is bonded to the nitrogen atom of the β-lactam ring and T denotes hydrogen, alkyl—CO—O—, pyridinium, 4-carbox-amidopyridinium, aminopyridinium, carbamoyloxy, azido, cyano, hydroxyl, the group —S—phenyl, which is optionally substituted, or the group —S—Het, in which Het denotes an optionally substituted heterocyclic 5-membered or 6-membered ring;

and in which

E denotes hydrogen, a pharmaceutically usable ester grouping, for example, the pivaloyl group, a salt-forming cation or a suitable protective group;

in which the compound of the formula I exists in either of the two possible R and S configurations, with respect to the chirality center C, or is a mixture of the diastereomers resulting therefrom, and if Z represents the group

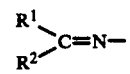

and $R^1$ and $R^2$ are different, the compound of formula (I) is optionally either in syn-form or in the anti-form, with respect to the imino group.

Furthermore, it has been found that the new β-lactam antibiotics of the formula I are obtained when compounds of the formula II

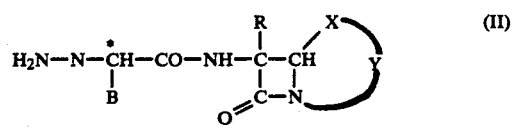

in which

R, B, C, X and Y have the meaning indicated above, or salts thereof, are reacted with compounds of the formula III

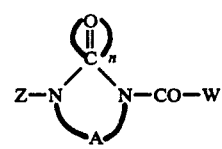

in which

Z and A have the meaning indicated above and

W represents halogen, azide or another nucleofugic leaving group, in the presence of a solvent and optionally of an acid-binding agent at temperatures from about −20° C. to about +50° C., and the resulting β-lactam antibiotics are optionally converted into their pharmaceutically usable salts or esters, or, if desired, the free acids are prepared from the resulting salts.

The compounds of the formula (I) according to the invention in which R represents lower alkoxy can also be prepared by alkoxylating the corresponding hydrogen derivatives (R=H), it being advantageous to use those compounds in which E denotes a suitable protective group in the alkoxylation.

In particular such a process is one in which a compound of the general formula

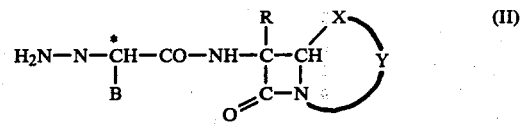

in which R, B, C, X and Y have the meaning indicated above, or salts thereof, is reacted with a compound of the general formula

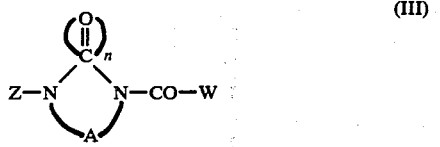

in which

Z, n and A have the meaning indicated above and

W denotes halogen, azide or another nucleofugic leaving group, in the presence of a solvent and optionally an acid-binding agent at a temperature of between −20° C. and +50° C., and the resulting β-lactam antibiotic is, if desired, converted into a pharmaceutically usable salt or an ester thereof, or, if desired, the free acid is prepared from the resulting salt.

In addition to good tolerance and solubility, the compounds according to the invention exhibit a broad antibacterial action, that is to say action against several families of bacteria in the Gram-negative range and against β-lactamase-forming bacteria. Because of their powerful antibacterial properties and because of their ability to improve the growth and feedstuff utilization of animals, the compounds according to the invention thus represent an advance in the art.

If, for example, α-amino-furfurylacetylpenicillin and 1-chlorocarbonyl-3-furfurylideneamino-imidazolidin-2-one are used as starting materials, the course of the reaction can be represented by the following equation:

In the general formulae, optionally substituted alkyl $R^1$ and $R^2$ is straight-chain or branched alkyl with preferably 1 to 6, in particular 1 to 4, carbon atoms. Examples which may be mentioned are optionally substituted methyl, ethyl, n- and i-propyl and n-, i- and t-butyl.

Optionally substituted alkenyl $R^1$ and $R^2$ is straight-chain or branched alkenyl with preferably 2 to 6, in particular 2 to 4, carbon atoms. Examples which may be mentioned are optionally substituted ethenyl, propen-1-yl, propen-2-yl, buten-3-yl and buten-2-yl-.

Optionally substituted cycloalkyl, cycloalkenyl and cycloalkadienyl $R^1$ and $R^2$ are monocyclic, bicyclic and tricyclic and preferably contain 3 to 10, in particular 3, 5 or 6, carbon atoms. Examples which may be mentioned are optionally substituted cyclopropyl, cyclobutyl, cyclobutenyl cyclopentyl, cyclopentenyl, cyclohexyl, cyclohexenyl, cyclohexadienyl, cycloheptyl, bicyclo-[2.2.1]-heptyl, bicyclo-[2.2.2]-octyl and adamantyl.

Optionally substituted aryl $R^1$ and $R^2$ is aryl with preferably 6 to 10 carbon atoms in the aryl part. Examples which may be mentioned are optionally substituted phenyl or naphthyl. Substituents in the phenyl ring are in the o-, m- or p-position. The radicals

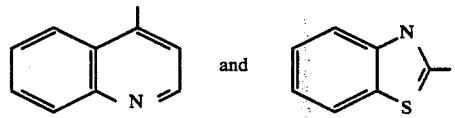

may also be mentioned.

Optionally substituted aralkyl $R^1$ and $R^2$ is aralkyl, which is optionally substituted in the aryl part and/or alkyl part, with preferably 6 or 10, in particular 6, carbon atoms in the aryl part and preferably 1 to 4, in particular 1 or 2, carbon atoms in the alkyl part, it being possible for the alkyl part to be straight-chain or branched. Examples which may be mentioned are optionally substituted benzyl and phenylethyl.

Optionally substituted heterocyclyl $R^1$ and $R^2$ are hetero-paraffinic, hetero-aromatic and hetero-olefinic 5-membered to 7-membered, preferably 5-membered or 6-membered, rings with preferably 1 to 3, in particular 1 or 2, identical or different hetero-atoms. Hetero-atoms are oxygen, sulphur or nitrogen. Examples which may be mentioned are optionally substituted thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazi-

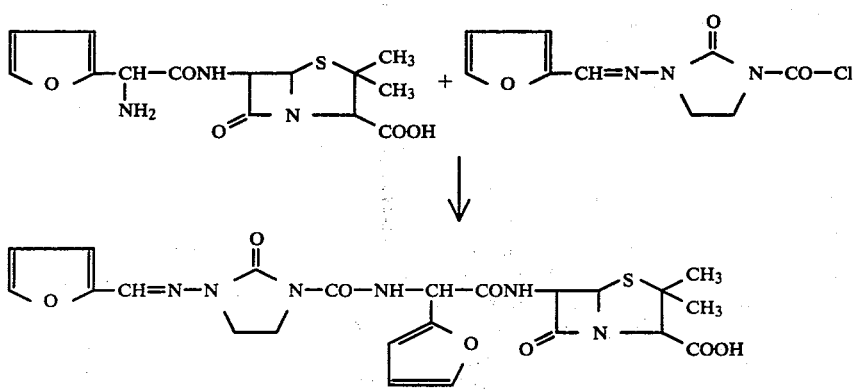

nyl, pyrimidinyl, tetrahydrofuranyl, dioxanyl, pyrrolidinyl, piperidinyl, morpholinyl, pyron-2-yl and pyron-4-yl.

Alkyl, alkenyl cycloalkyl, cycloalkenyl, cycloalkadienyl, aryl and aralkyl $R^1$ and $R^2$ can carry one or more, preferably 1 to 3 and in particular 1 or 2, identical or different radicals $R^3$. Very particularly preferably, the radicals $R^1$ and $R^2$ mentioned are unsubstituted or contain one substituent $R^3$.

Heterocyclyl $R^1$ and $R^2$ can carry one or more, preferably 1 to 3 and in particular 1 or 2, identical or different radicals $R^4$. Very particularly preferably, heterocyclyl $R^1$ and $R^2$ is unsubstituted or contains one substituent $R^4$.

In the following statements, the expression "lower alkyl" in all cases, also in connection with other atoms or groups (for example lower alkoxy, $$\overset{|}{\text{HCON}-}$$

(lower alkyl) and the like) denotes straight-chain or branched alkyl with preferably 1 to 6, in particular 1 to 4, carbon atoms. Examples which may be mentioned are optionally substituted methyl, ethyl, n- and i-propyl and n-, i- and t-butyl. "Lower alkyl" can be substituted by 1 to 5, in particular 1 to 3, identical or different halogen atoms, halogen atoms being, preferably, fluorine, chlorine and bromine, especially fluorine and chlorine. Examples which may be mentioned are trifluoromethyl, chloro-di-fluoromethyl, bromomethyl, 2,2,2-tri-fluoroethyl and pentafluoroethyl.

$R^3$ preferably denotes halogen, preferably fluorine, chlorine, bromine and iodine, especially fluorine, chlorine and bromine; amino; mono-lower alkylamino, preferably methylamino and ethylamino, especially methylamino; di-lower alkylamino, preferably dimethylamino and diethylamino, especially dimethylamino; pyrrolidyl; piperidyl; HCO—NH—; lower alkyl—CO—NH—, preferably $CH_3$—CO—NH—; H—CO—N(lower alkyl)—, preferably H—CO—N($CH_3$)— and H—CO—N($C_2H_5$)—; lower alkyl—CO—N(lower alkyl)—, preferably $CH_3$—CO—N($CH_3$)—; (lower alkyl)$_2$C=N—; lower alkyl—$SO_2$—NH—, preferably $CH_3$—$SO_2$—NH— and $C_2H_5$—$SO_2$—NH—, especially $CH_3$—$SO_2$—NH—; lower alkyl—$SO_2$—N(lower alkyl)—, preferably $CH_3$—$SO_2$—N($CH_3$)—; HO—$SO_2$—NH—; HO—$SO_2$—N(lower alkyl)—, preferably HO—$SO_2$—N($CH_3$)— and HO—$SO_2$—N($C_2H_5$)—; amidino; (lower alkyl)$_2$—N—CH=N—, in particular $(CH_3)_2$N—CH=N—;

guanido, nitro, azido, hydroxyl and lower alkyloxy—, preferably $CH_3$—O—, and $C_2H_5$—O—, especially $CH_3O$—; H—CO—O— and lower alkyl—CO—O—, preferably $CH_3$—CO—O, $C_2H_5$—CO—O— and $(CH_3)_3C$—CO—O—; lower alkyl—O—CO—O—, preferably $CH_3$—O—CO—O—, $C_2H_5$—O—CO—O— and $(CH_3)_3C$—O—CO—O—; $H_2N$—CO—O—; lower alkyl—NH—CO—O—, preferably $CH_3$—NH—CO—O— and $C_2H_5$—NH—CO—O—; (lower alkyl)$_2$N—CO—O—, preferably $(CH_3)_2$—CO—O— and $(C_2H_5)_2$N—CO—O,

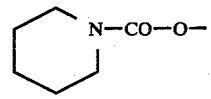

and $H_2N$—$SO_2$—O—; lower alkyl—NH—$SO_2$—O—, preferably $CH_3$—NH—$SO_2$—O— and $C_2H_5$—NH—$SO_2$—O—; (lower alkyl)$_2$ N—$SO_2$—O—, preferably $(CH_3)_2$ N—$SO_2$—O— and $(C_2H_5)_2$ N—$SO_2$—O—; HOOC— and $H_2N$—CO—; (lower alkyl)$_2$N—CO—; in particular $(CH_3)_2$N—CO— and $(C_2H_5)_2$N—CO—; OHC—, HO—SO—O— and HS—; lower alkyl—S—, preferably $CH_3$—S—, $CF_3$—S—, $C_2H_5$—S— and $(CH_3)_2$CH—S—;

lower alkyl-S—,
‖
O preferably

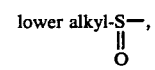

and $C_2H_5$—S—;
‖
O $HO_3S$—; lower alkyl—$SO_2$—, preferably $CH_3$—$SO_2$—, $CF_3SO_2$— and $C_2H_5$—$SO_2$—; the group $H_2N$—$SO_2$—; lower alkyl—NH—$SO_2$—, preferably $CH_3$—NH—$SO_2$— and $C_2H_5$—NH—$SO_2$—; (lower alkyl)$_2$N—$SO_2$—, preferably $(CH_3)_2$ N—$SO_2$— and $(C_2H_5)_2$ (N—$SO_2$—;

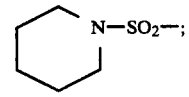

the group HO—$SO_2$—S—; straight-chain or branched alkyl with 1 to 6 carbon atoms, in particular methyl, ethyl, propyl, isopropyl, n-butyl, sec.-butyl or tert.-butyl, preferably methyl; and phenyl or phenoxy.

In the case where $R^4$ is on one or more carbon atoms in the heterocyclyl $R^1$ and $R^2$, $R^4$ preferably denotes lower alkyl, preferably methyl, ethyl and isopropyl, especially methyl; the trifluoromethyl group; halogen, preferably fluorine, chlorine and bromine; amino; lower alkylamino, preferably $CH_3$—NH— and $C_2H_5$—NH—; di-lower alkylamino, preferably $(CH_3)_2$N— and $(C_2H_5)_2$N—; formylamino; acetylamino; $CH_3$—O—CO—NH—, and $C_2H_5O$—CO—NH—; $CH_3$—$SO_2$—NH—; hydroxyl; methoxy and ethoxy; methylthio and ethylthio; $CH_3$—$SO_2$—; $CH_3$—SO—; and the groups HOOC—; $HO_3S$—; HCO—; lower alkyl—CO—, preferably $CH_3$—CO—; lower alkyl—O—CO—, preferably $CH_3$—O—CO— and $C_2H_4O$—CO—; and —CN.

In the case where $R^4$, as a substituent, in a nitrogen-containing heterocyclyl $R^1$ and $R^2$ is on one or more nitrogen atoms, $R^4$ preferably denotes lower alkyl, preferably methyl, ethyl, propyl and isopropyl, especially methyl and ethyl; the group —C≡N; —CHO; —COO—lower alkyl, preferably —COO—CH$_3$, —COOC$_2$H$_5$, —COOCH(CH$_3$)$_2$ and —COO—C(CH$_3$)$_3$; —CO—NH$_2$; —CO—NH—lower alkyl, preferably —CO—NH—CH$_3$, —CO—NH—C$_2$H$_5$ and —CO—NH—CH(CH$_3$)$_2$; and —CO—lower alkyl, preferably —CO—CH$_3$, —CO—C$_2$H$_5$ and —CO—CH(CH$_3$)$_2$.

The rings which can be formed by $R^1$ and $R^2$, together with the carbon atom to which they are bonded, are saturated or unsaturated. Unsaturated rings preferably contain 1 or 2 double bonds. The rings can contain 1 or more, preferably 1 or 2 and in particular 1, hetero-atom or hetero-group. Hetero-atoms which may be mentioned are oxygen, sulphur and/or nitrogen. Examples of hetero-groups which may be mentioned are the SO$_2$— group and the lower alkyl—N— group, and in the case of 6-membered rings, a hetero-atom or a hetero-group is preferably in the 4-position (relative to the carbon atom to which $R^1$ and $R^2$ are bonded). Particularly preferred rings which may be mentioned are:

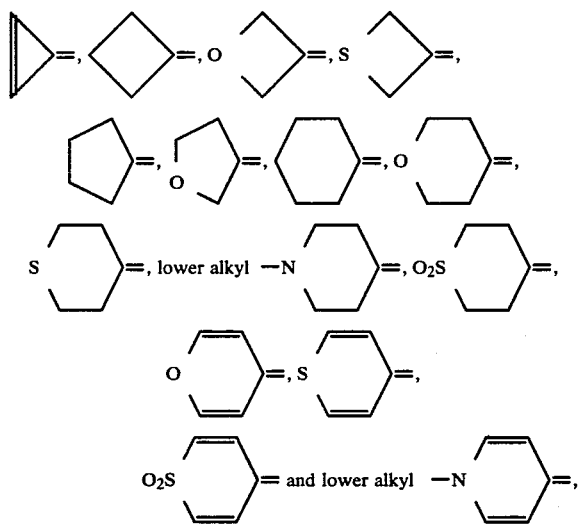

The rings which are formed by $R^1$ and $R^2$, together with the carbon atom to which they are bonded, can contain one or more, preferably 1 to 3 and in particular 1 or 2, identical or different substituents $R^5$. $R^5$ preferably denotes halogen, preferably fluorine, chlorine, and bromine; hydroxyl; lower alkoxy, preferably methoxy and ethoxy; lower alkylthio, preferably methylthio and ethylthio; amino; lower alkylamino, preferably CH$_3$—NH— and C$_2$H$_5$—NH—; di-lower alkylamino preferably dimethylamino and diethylamino; the groups —CN; —COOH; and —COOCH$_3$ and —COOC$_2$H$_5$; and straight-chain or branched lower alkyl, preferably methyl and ethyl.

At least one of the radicals $R^1$ and $R^2$ particularly preferably represents hydrogen.

Z particularly preferably represents the group

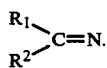

Compounds which contain the radical

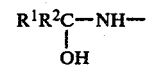

are formed when the compounds of the formula III already contain this radical, or can be formed when the reaction is carried out in water-containing solvents.

B preferably represents a saturated or unsaturated, but preferably unsaturated, optionally substituted hetero-cyclic radical, which can contain 1 to 4, preferably 1 to 3, identical or different hetero-atoms from the series oxygen, sulphur and/or nitrogen.

Examples of suitable radicals of this type which may be mentioned are: pyrazolyl, imidazolyl, oxazolyl, oxdiazolyl, 2-amino- and 2-oxo-Δ$^4$-thiazolinyl, tetrazolyl and sydnonyl, as well as the furyl, thienyl, pyrrolyl, thiazolyl, isothiazolyl, isoxazolyl and thiadiazolyl radicals, which are particularly valuable within the scope of this invention. The heterocyclic radical B can carry one or more, preferably 1 to 2, in particular 2 identical or different substituents. Examples of substituents which may be mentioned are halogen, such as fluorine, chlorine and bromine, preferably fluorine and chlorine, alkyl with 1 to 6, preferably 1 to 4 and in particular 1 or 2, carbon atoms, cyano, sulpho and methylsulphonyl.

In the definition of T, alkyl in alkyl—CO—O— preferably denotes alkyl with 1 to 4, in particular 1 or 2, carbon atoms. Examples which may be mentioned are methyl and ethyl, methyl being particularly preferred.

The heterocyclic ring Het in —S—Het (definition of T) consists of 5 or 6 ring members and contains 1 to 4, preferably 1 to 3, identical or different hetero-atoms, hetero-atoms being oxygen, sulphur and nitrogen. The heterocyclic ring is preferably unsaturated and particularly preferably contains 2 double bonds. The heterocyclic ring can contain one or more, preferably 1 or 2 and in particular one, substituent. Examples of substituents which may be mentioned are: halogen, such as fluorine, chlorine and bromine, preferably chlorine and bromine, amino, lower alkylamino, di-lower alkylamino, lower alkyl, cycloalkyl (with 3 to 7, preferably 5 or 6, carbon atoms in the cycloalkyl part), lower alkoxy (for the meaning of "lower alkyl" see above), trifluoromethyl, phenyl, benzyl and acylamino with preferably 2 to 5, in particular 2 or 3, carbon atoms. Particularly preferred —S—Het which may be mentioned are:

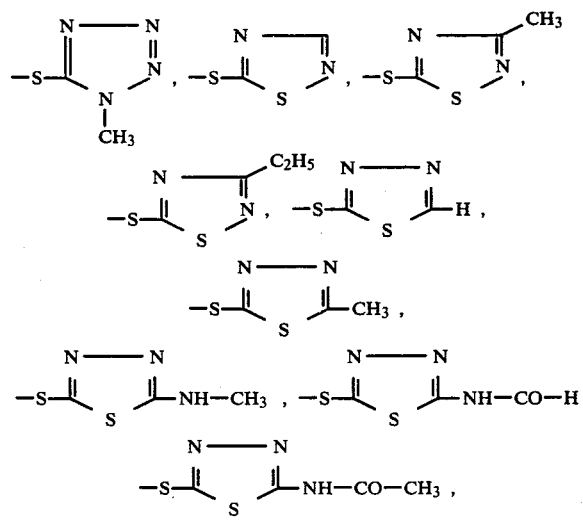

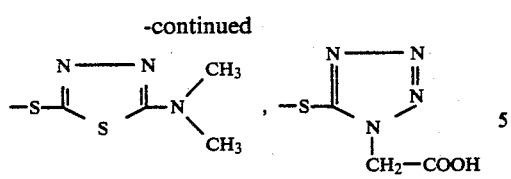
, 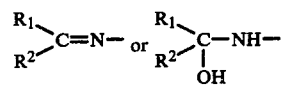

The -S-phenyl radial in the definition of T can carry one or more, preferably 1 to 3 and in particular 1 or 2, identical or different substituents, preferred substituents being those which are listed above as possible substituents of the radial -S-Het.

R in the meaning of lower alkoxy preferably designates an alkoxy group with 1 to 6, in particular 1 to 4, carbon atoms, but in particular methoxy or ethoxy.

Compounds according to the invention in which C is in the D=R configuration are very particularly preferred.

All the crystal forms and hydrate forms of the compounds of the general formula (I) according to the invention, and of their salts, are antibacterially active in the same way.

Halogen W represents fluorine, chlorine and bromine, preferably bromine or chlorine, especially chlorine.

By nucleofugic leaving groups in the definition of W there are to be understood all the nucleofugic groups customarily used in organic chemistry, and above all those which are described in Angewandte Chemie, 81 (1969), page 543.

In the preparation, the compounds of the formula (I) are in many cases obtained in the form of salts, or they can be readily converted into these. The pharmaceutically usable salts of the compounds according to formula (I) are particularly important for use as medicaments.

Pharmaceutically usable salts of the compounds of the formula (I) are salts of these compounds with inorganic and organic bases on the acid carboxyl group or the acid carboxyl and sulphonic acid groups. Bases which can be employed for this are all the bases customarily used in pharmaceutical chemistry, in particular in the chemistry of antibiotics. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate and sodium bicarbonate and potassium bicarbonate; and aluminum hydroxide and ammonium hydroxide. Organic bases which can be employed are primary, secondary and tertiary aliphatic amines as well as heterocyclic amines. Examples which may be mentioned are: di- and tri-lower alkylamines, for example diethylamine, triethylamine, tri-β-hydroxyethylamine, procaine, dibenzylamine, N, N'-dibenzylethylenediamine, N-benzyl-β-phenylethylamine, N-methyl- and N-ethylmorpholine, 1-ephenamine, dehydrobietylamine, N,N'-bis-dehydroabietylethylenediamine and N-lower alkylpiperidine. So-called basic aminoacids, such as lysine or arginine can also be advantageously used as bases. Particularly preferred salts are the sodium salts.

Very particularly preferred compounds of the formula I are those in which the definition of the radicals is as follows:

R represents hydrogen or methoxy;
Z represents the groups

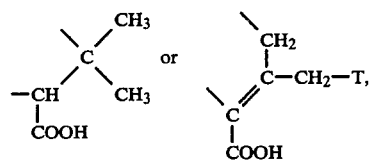

in which $R^1$ denotes hydrogen; and $R^2$ denotes phenyl which is optionally substituted by halogen (in particular fluorine, chlorine and bromine), alkyl with 1 to 4 carbon atoms (in particular methyl), alkoxy with 1 to 4 carbon atoms (in particular methoxy), nitro, cyano, alkylsulphonyl with 1 to 4 carbon atoms (in particular methylsulphonyl) or $CH_3OOC-$, or denotes furyl or thienyl which is optionally substituted, preferably in the 4-position or 5-position, by halogen (in particular chlorine or bromine), $NO_2$, alkyl or alkoxycarbonyl with 1 to 4 carbon atoms or $CH_3COOCH_2-$, the furyl and thienyl ring preferably being bonded in the 2-position or 3-position; or pyridyl (preferably pyrid-3-yl); or represents optionally substituted straight-chain, branched or cyclic alkyl or alkenyl with up to 7 carbon atoms, in particular cyclohexyl or alkyl or alkenyl with up to 4 carbon atoms, the alkyl and alkenyl groups mentioned being optionally substituted, possible preferred substituents being halogen and alkoxy with 1 to 4 carbon atoms, in particular methoxy; and A represents $-CH_2-CH_2-$;

B represents furyl, thienyl, pyrrolyl, imidazolyl, thiazolyl, isothiazolyl, isoxazolyl and thiadiazolyl and Y represents the groups $$\begin{array}{c} CH_3 \\ \diagdown / \\ C \\ / \diagdown \\ -CH \quad CH_3 \\ | \\ COOH \end{array} \quad \text{or} \quad \begin{array}{c} \diagdown \\ CH_2 \\ | \\ C-CH_2-T, \\ \diagup \\ C \\ | \\ COOH \end{array}$$

in which

T represents hydrogen, $-O-CO-CH_3$, hydroxyl or thiadiazolylthio or tetrazolylthio which is optionally substituted by alkyl with 1 to 4 carbon atoms or $CF_3$; and C is in the D=R configuration; and the sodium salts of these compounds.

Compounds of the general formula II used as starting materials are already known and are obtainable by known methods. (Compare DOS(German Published Specification) No. 2,555,159).

All the crystal forms, hydrate forms and salts of the compounds of the general formula II are suitable starting materials for the process according to the invention.

Examples which may be mentioned are: α-amino-furfuryl-acetyl-penicillin and 7-(α-amino-furfurylacetamido-)3-acetoxy-methyl-ceph-3-em-4-carboxylic acid.

Salts of the compounds of the formula II which can be employed are preferably salts with bases which have been mentioned as suitable for salt formation with compounds of the formula I. The sodium salts are particularly preferred.

The compounds of the general formula III used as starting materials are obtainable by known methods.

They can be obtained, for example, by the following route (compare also J.A.C.S. 78 (1956) 5349):

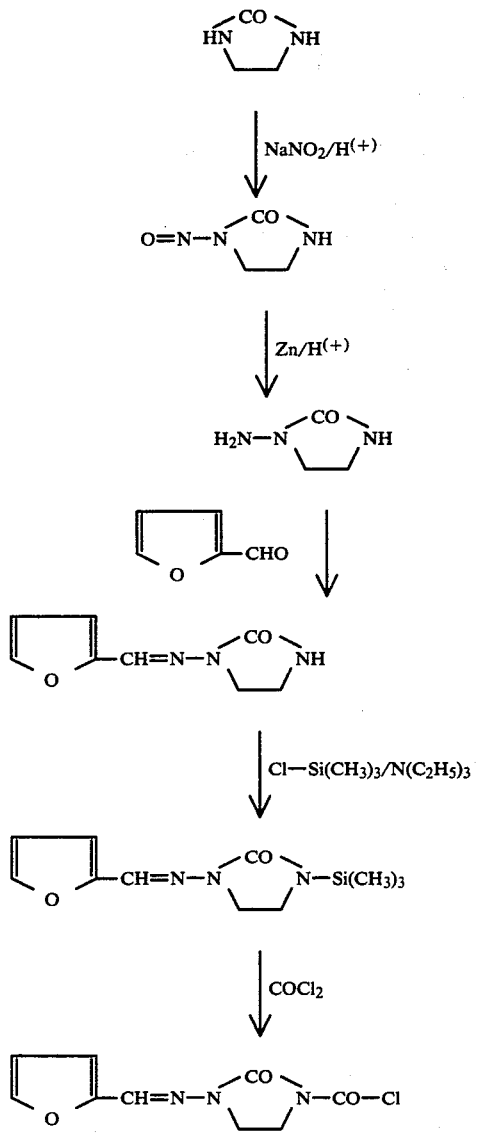

It is also possible to carry out the phosgenation directly in an inert organic solvent in the presence of a base, without prior silylation.

Examples which may be mentioned of starting compounds of the general formula (III) according to the invention are: 1-chlorocarbonyl-2-oxo-3-furfurylidene-amino-imidazolidine, 1-azidocarbonyl-2-oxo-3-furfurylidene-amino-imidazolidine and 1-chlorocarbonyl-2-oxo-3-crotonylideneamino-imidazolidine.

Those compounds of the general formula (III) in which W is azide are obtained in the customary manner, for example from the corresponding compounds (III), in which W is halogen, by reaction with, for example, alkali metal azides.

Possible diluents in the process according to the invention are water and all the inert organic solvents, preferably those which are water-miscible. These include, above all, lower dialkylketones, for example acetone and methyl ethyl ketone, and cyclic ethers, for example tetrahydrofuran and dioxane; nitriles, for example acetonitrile; lower dialkylformamides, for example dimethylformamide; lower alkyl alcohols, for example ethanol and isopropanol, as well as dimethylsulphoxide. These solvents can also be used in mixtures with one another and in any desired mixtures of one or more of these solvents with water. The process according to the invention can thus be carried out in the presence of: (a) exclusively water, (b) exclusively one or more organic solvents or (c) water and one or more organic solvents. If, because of the presence of water, a PH measurement is possible during the reaction according to the invention, the pH of the reaction mixture is preferably kept between 6.5 and 7.5 by adding bases or by using buffer mixtures. However, the process according to the invention can also be carried out very well in another pH range, for example between 4.5 and 9.0 or at pH 2.0 to 4.5. Furthermore, it is possible to carry out the reaction in water-immiscible solvents, for example halogenated hydrocarbons, such as chloroform or methylene chloride, organic bases being added, preferably lower alkylamines, for example triethylamine or diethylamine, or cyclic bases, for example N-ethylpiperidine. Moreover, the reaction can be carried out in a mixture of water and a water-immiscible solvent, such as, for example, lower alkyl ethers, such as diethyl ether, halogenated hydrocarbons, such as chloroform and methylene chloride; carbon bisulphide; isobutyl methyl ketone; esters, such as ethyl acetate; and aromatic hydrocarbons, such as benzene, it being appropriate to stir the mixture vigorously and to keep the pH value between 4.5 and 9.0 or, for example, 2.0 and 4.5 by adding bases or using customary buffer solutions, for example phosphate buffer, acetate buffer or citrate buffer. However, it is also possible to carry out the reaction in water alone in the absence of organic solvents, in the presence of an organic or inorganic base or with the addition of customary buffer substances.

All the acid-binding agents customarily used in the chemistry of antibiotics can be employed as the acid-binding agent. These include inorganic bases and organic bases, which, for example because of steric hindrance, are difficult to acylate. Examples of inorganic bases which may be mentioned are sodium hydroxide and potassium hydroxide. Possible organic bases are virtually all the open-chain or cyclic amines which cannot be acylated or are difficult to acylate, and also hetero-aromatic bases. Examples of bases which may be mentioned are tertiary amines, preferably lower alkylamines, for example triethylamine, and/or cyclic bases, for example pyridine, as well as the secondary amine dicyclohexylamine, which is difficult to acylate.

It is only necessary to add a base in the process according to the invention if acid compounds are formed during the reaction, for example in the case where W represents halogen or azide.

The reaction temperatures can be varied within a relatively wide range. Preferably the reaction is carried out between $-20°$ C. and $+50°$ C., more preferably between 0 and $+20°$ C. However, as in the case of most chemical reactions, higher or lower temperatures can also be used.

The reaction can be carried out under normal pressure, but also under reduced or increased pressure. Usually it is carried out under normal pressure.

The proportions of the reactants of the formula (II) and (III) can be varied within wide limits in carrying out the process according to the invention, without adversely influencing the result. The starting materials can be reacted with one another in, for example, equimolar amounts. However, it can be appropriate to use one of the two reactants in excess, in order to make the purification of the desired antibiotic or its preparation in a pure form easier and to increase the yield.

It is possible, for example, to employ the reactants of the general formula II in an excess of 0.1 to 0.3 molar equivalent and thereby to achieve less decomposition of the reactants of the general formula III in a water-containing solvent mixture. Because of their good solubility in aqueous mineral acids, the excess of the reactants of the general formula II can be easily removed during working up of the reaction mixture.

On the other hand, however, the reactants of the general formula III can also be advantageously employed in an excess of, for example, 0.1 to 1.0 molar equivalents. The reactants of the general formula II are thereby better utilized, and the decomposition of the reactants of the general formula III, which proceeds as a side-reaction in water-containing solvents, is compensated for. Since the compounds of the general formula III added in excess are rapidly converted in water into neutral nitrogen-containing heterocyclic compounds, which can be easily removed, the purity of the antibiotics is thereby scarcely impaired.

The amount of bases optionally used is determined, for example, by the particular pH value it is desired to maintain. If pH measurement and adjustment are not carried out or, because sufficient amounts of water are lacking in the diluent, are not possible, or not appropriate, 2 molar equivalents of base are preferably added.

The reaction mixtures for the preparation of the compounds according to the invention, and their salts, are without exception worked up in the manner which is generally known for these substances. The isolation and purification of the compounds according to the invention and the liberation of the free acids from salts or the conversion of the free acids into salts are also carried out by customary methods of organic chemistry.

Alternatively, the compounds of the formula (I) in which R denotes lower alkoxy are also obtainable by alkoxylating the corresponding hydrogen derivatives (R=H), E denoting a suitable protective group, such as an easily removable ester-forming group, or an acetoxymethyl group, the cationic radical of a base, preferably of an alkali metal hydroxide or alkaline earth metal hydroxide, or hydrogen.

In this process, a β-lactam compound of the formula (I) in which R denotes hydrogen is reacted with 2–10 equivalents, per equivalent of β-lactam compound, of a base in the presence of an excess of an alcohol of the formula R'OH, in which R' designates lower alkyl, in an inert organic solvent, between 1 and 8 equivalents of a N-halogenating agent are added and the compound of the formula (I) in which R denotes lower alkoxy is isolated, if appropriate after first splitting off the acid-protective group, converting the acid into a salt or a pharmaceutically usable ester.

Compounds which transfer positively charged chlorine, such as t-butyl hypochlorite or chloroacetamide, are preferably used as the N-halogenating agent in this process according to the invention.

Suitable bases are complex and simple, but preferably simple, alkali metal hydrides and alkaline earth metal hydrides, metal-organic compounds and Grignard compounds. Examples which may be mentioned are: lithium hydride, sodium hydride, butyl-lithium, phenyl-lithium, alkyl-magnesium bromide, for example methyl-magnesium bromide, or other known acid-binding agents, such as alkali earth alcoholates or carbonates and alkaline earth metal alcoholates or carbonates, alkali metal bicarbonates or oxides and alkaline earth metal bicarbonates or oxides, such as, for example, sodium carbonate, or other acid-binding agents, such as borax, or open-chain or cyclic organic bases, such as trialkylamines or aralkylamines, or cyclic amidines, such as 2,3,4,6,7,8-hexahydro-pyrrolo[1,2-a]pyrimidine (DBN) or 2,3,4,6,7,8,9,10-octahydro-pyrimido[1,2-a]azepine (DBU).

Examples of suitable solvents are open-chain or cyclic ethers, aliphatic and aromatic hydrocarbons or halogenohydrocarbons or the alcohols R'OH. Tetrahydrofuran is particularly suitable.

The reaction temperatures are to be kept below 0° C. as far as possible, preferably between −70° C. and −45° C.

In the form of the free acid, the compounds of the general formula I are antibacterially active in the same manner both in the crystalline and amorphous forms and both in the anhydrous forms and the various hydrate forms. Likewise, in the form of their salts, for example the sodium salts, the compounds of the general formula I are antibacterially active in the same manner both in the crystalline and amorphous forms and both in the anhydrous and water-containing, for example the hydrate, forms.

Examples of new active compounds which may be mentioned are (formulae (IV) to (VII))

$$R^5 \underset{O}{\underset{\|}{\bigcirc}} CH=N-N \underset{\bigcirc}{\bigcirc} N-CO-NH-\underset{B}{\overset{}{C}H}-CO-NH-\underset{O}{\overset{R}{\underset{\|}{\bigcirc}}} \overset{S}{\underset{N}{\bigcirc}} \underset{COOH}{\overset{CH_3}{\underset{CH_3}{\bigcirc}}} \quad (IV)$$

| $R^5$ | B | R |
|---|---|---|
| H | Fur-2-yl | H |
| CH₃ | " | " |
| Cl | " | " |
| Br | " | " |
| H | " | CH₃O |
| H | Fur-3-yl | H |
| CH₃ | " | " |
| Cl | " | " |
| Br | " | " |
| H | " | CH₃O |
| H | Thien-2-yl | H |
| H | Thien-2-yl | OCH₃ |

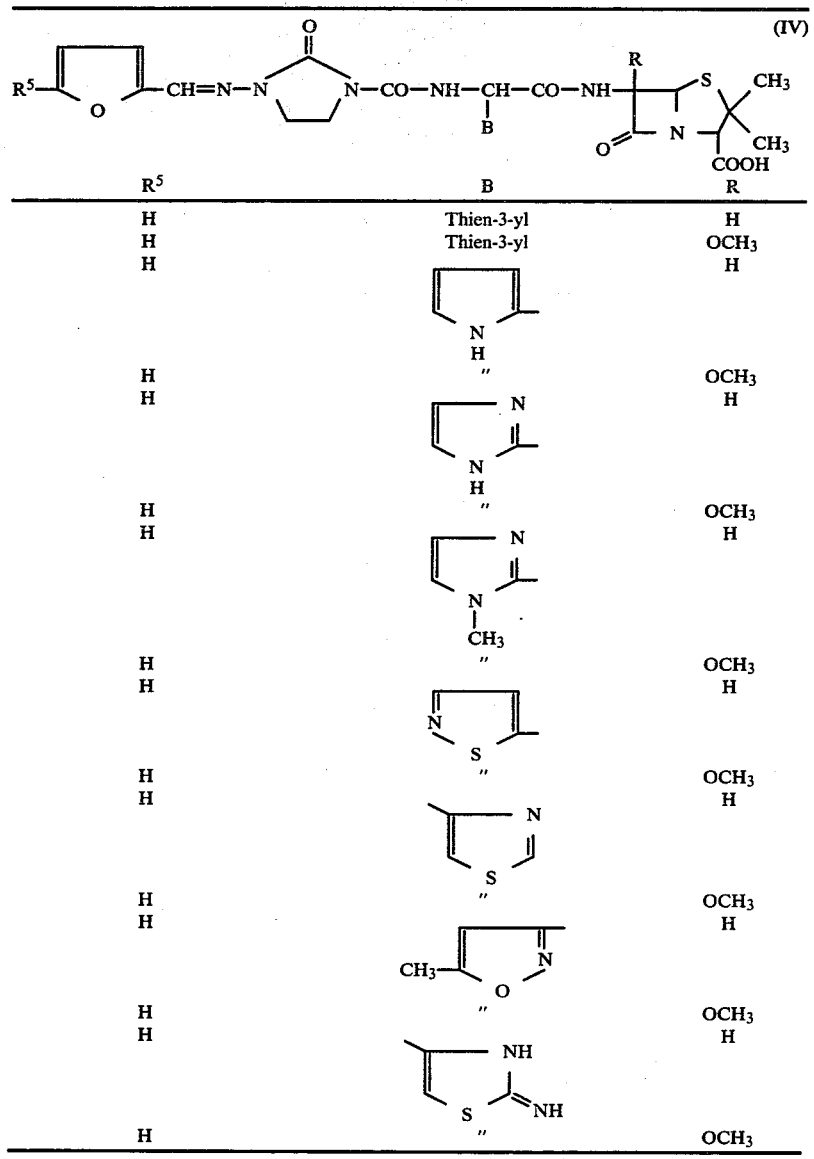
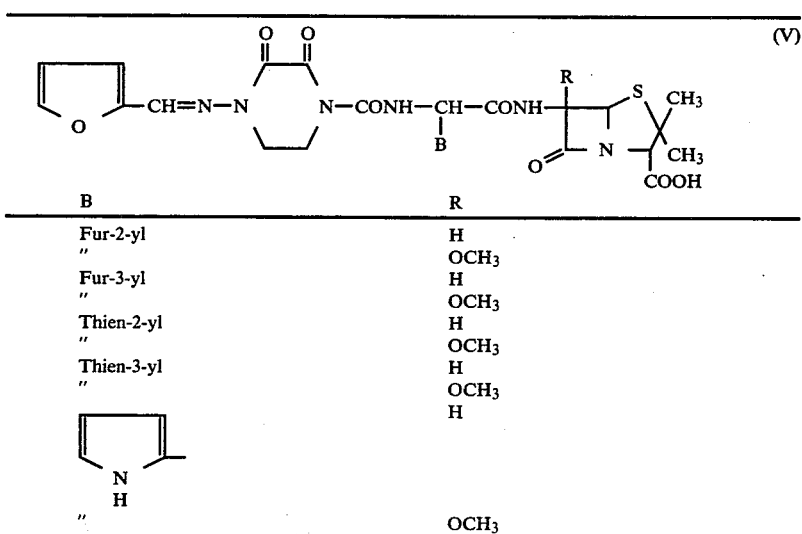

-continued
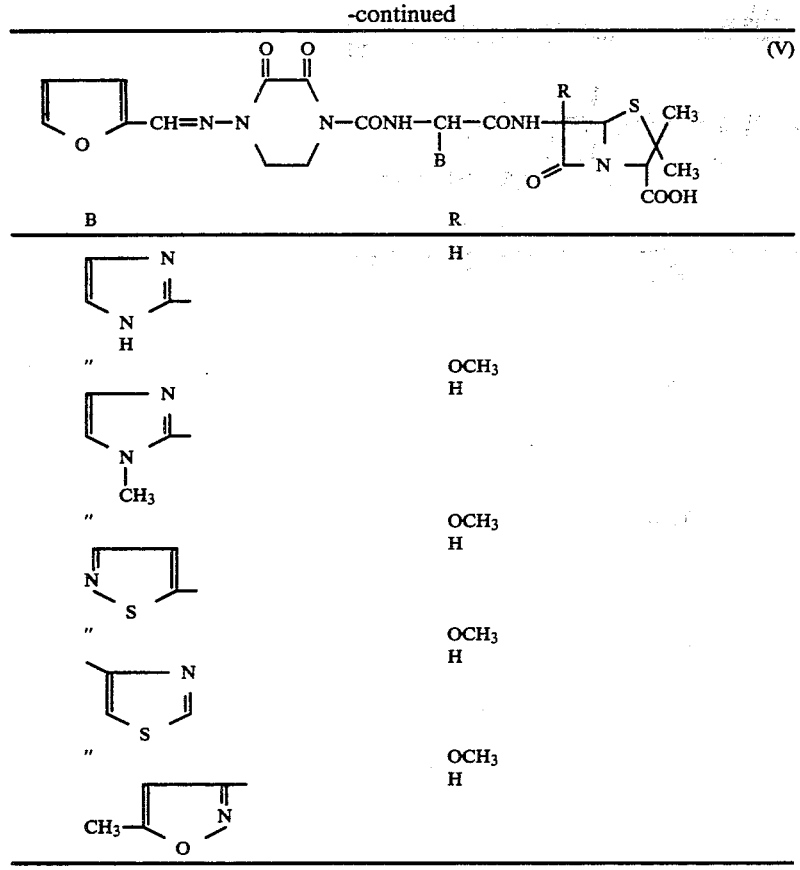
| B | R |
|---|---|
| imidazol-2-yl (NH) | H |
| " | OCH₃ |
| 1-methylimidazol-2-yl | H |
| " | OCH₃ |
| isothiazol-3-yl | H |
| " | OCH₃ |
| thiazol-4-yl | H |
| " | OCH₃ |
| 5-methylisoxazol-3-yl | H |
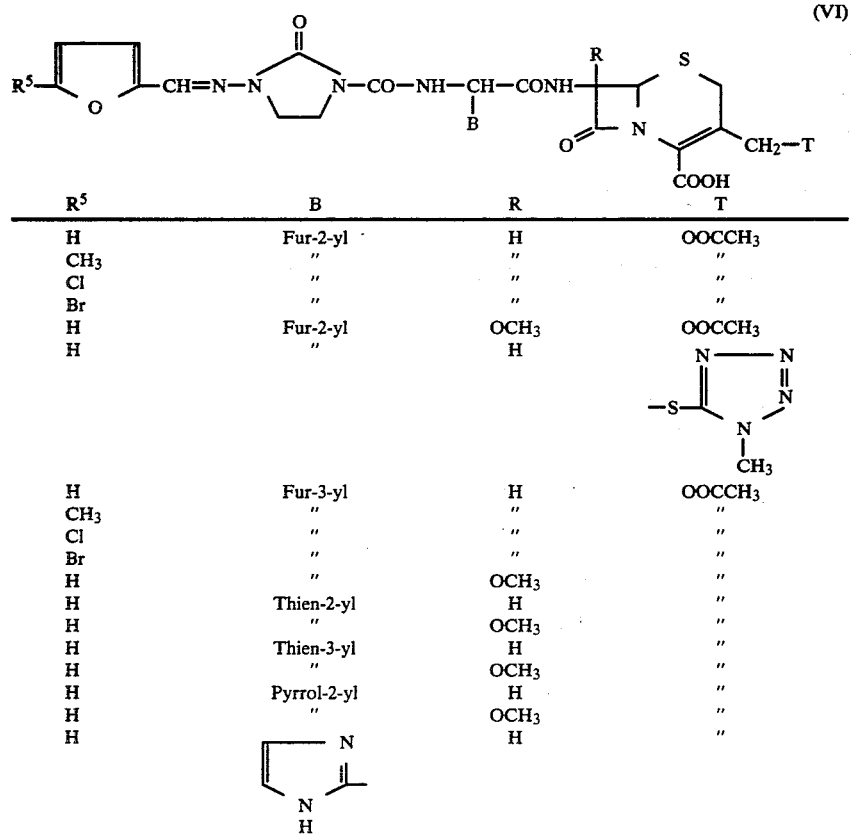
| R⁵ | B | R | T |
|---|---|---|---|
| H | Fur-2-yl | H | OOCCH₃ |
| CH₃ | " | " | " |
| Cl | " | " | " |
| Br | " | " | " |
| H | Fur-2-yl | OCH₃ | OOCCH₃ |
| H | " | H | —S—(1-methyltetrazol-5-yl) |
| H | Fur-3-yl | H | OOCCH₃ |
| CH₃ | " | " | " |
| Cl | " | " | " |
| Br | " | " | " |
| H | " | OCH₃ | " |
| H | Thien-2-yl | H | " |
| H | " | OCH₃ | " |
| H | Thien-3-yl | H | " |
| H | " | OCH₃ | " |
| H | Pyrrol-2-yl | H | " |
| H | " | OCH₃ | " |
| H | imidazol-2-yl (NH) | H | " |

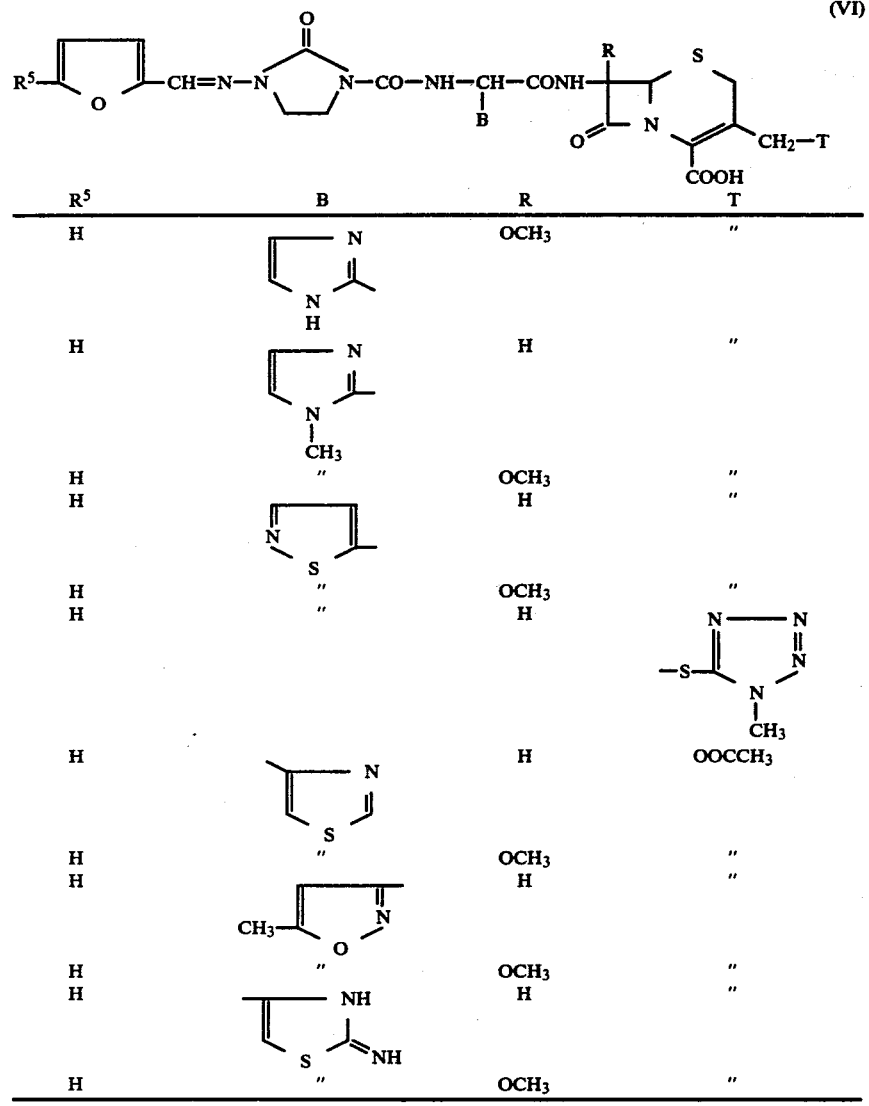
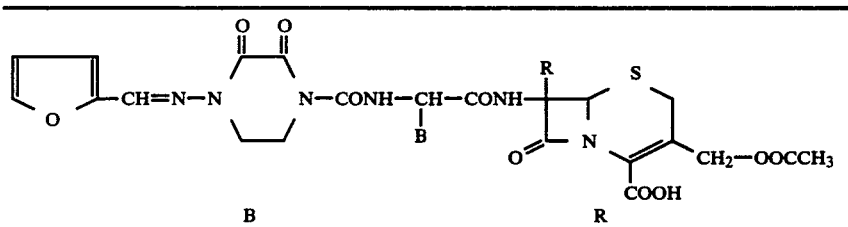
| B | R |
|---|---|
| Furyl-2 | H |
| Furyl-2 | OCH₃ |
| Furyl-3 | H |
| Furyl-3 | OCH₃ |
| Thienyl-2 | H |
| Thienyl-2 | OCH₃ |
| Thienyl-3 | H |
| Thienyl-3 | OCH₃ |
| Pyrrolyl-2 | H |
| Pyrrolyl-2 | OCH₃ |
| 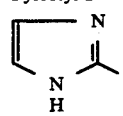 | H |

-continued

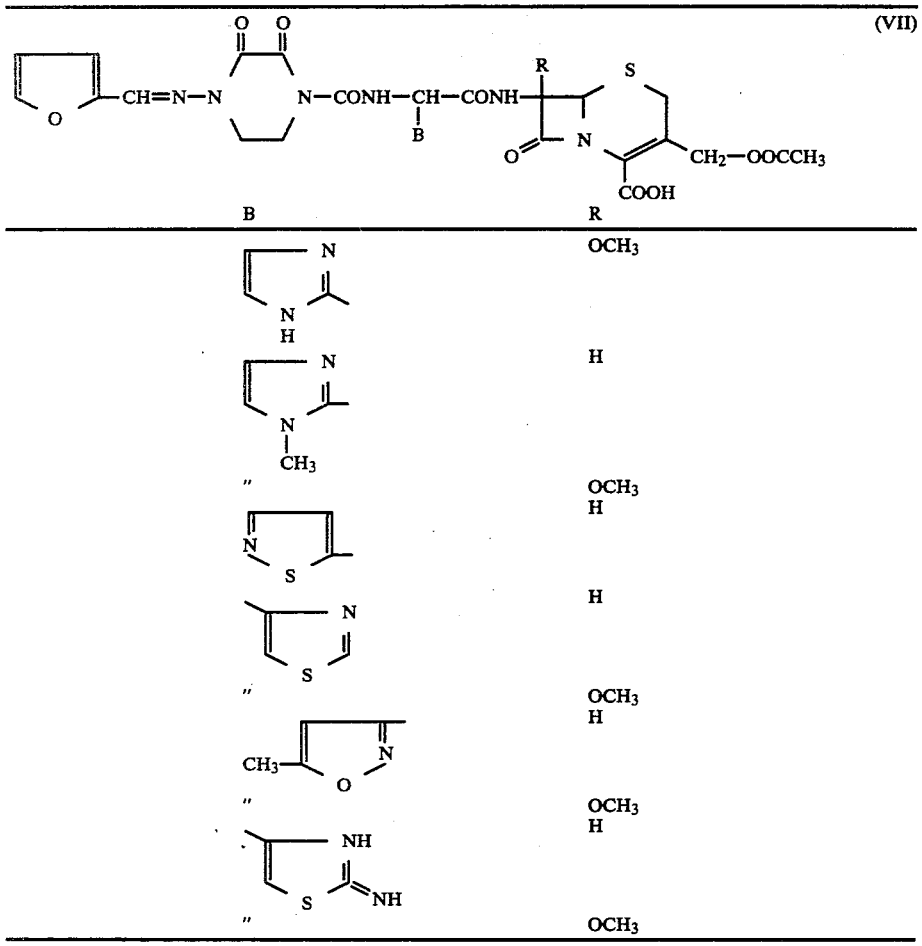

The active compounds according to the invention display a powerful and broad antimicrobial action, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

The active compounds according to the invention are active against a very broad spectrum of microorganisms. With their aid it is possible to combat, for example, Gram-negative and Gram-positive bacteria and bacteria-like micro-organisms and to prevent, alleviate and/or cure diseases caused by these pathogens.

The active compounds according to the invention are particularly active against bacteria and bacteria-like micro-organisms. They are therefore particularly suitable, in human medicine and veterinary medicine, for the prophylaxis and chemotherapy of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus*, *Staph. epidermidis* and *Staph. aerogenes*, and *Gaffkya tetragena* (Staph.=Staphylococcus);

Lactobacteriaceae, such as Streptococci, for example *Streptococcus pyogenes*, α- and β-haemolysing Streptococci, non-(γ-)-haemolysing Streptococci, *Str. viridans*, *Str. faecalis* (Enterococci), *Str. agalactiae*, *Str. lactis*, *Str. equi* and *Str. anaerobis*, and *Diplococcus pneumoniae* (Pneumocci) (Str.=Streptococcus);

Neisseriaceae, such as Neisseriae, for example *Neisseria gonorrhoeae* (Gonococci), *N. meningitidis* (Meningococci), *N. catarrhalis* and *N. flava* (N.=Neisseria);

Corynebacteriaceae, such as Corynebacteria, for example *Corynebacterium diphtheriae*, *C. pyogenes*, *C. diptheroides*, *C. acnes*, *C. parvum*, *C. bovis*, *C. renale*, *C. ovis* and *C. murisepticum* (C=Corynebacterium);

Mycobacteriacae, such as pathogens of Mycobacterioses, for example *Mycobacterium tuberculosis*, *M. bovis*, *M. avium*, so-called atypical mycobacteria of Runyon groups I, II, III and IV and *M. leprae* (M.=Mycobacterium);

Enterobacteriaceae, such as *Escherichiae* bacteria of the Coli group: Escherichia bacteria, for example *Escherichia coli*, Enterobacter bacteria, for example *E. aerogenes* and *E. cloacae*, Klebsiella bacteria, for example, *K. pneumoniae* and *K. ozaenae*, Erwiniae, for example Erwinia spec., and Serratia, for example *Serratia marcescens*, (E.=Enterobacter) (K.=Klebsiella), Proteae bacteria of the Proteus group: Proteus, for example *Proteus vulgaris*, *Pr. morganii*, *Pr. rettgeri* and *Pr. mirabilis*, and Providencia, for example Providencia sp., (Pr.=Proteus), Salmonelleae: Salmonella bacteria, for example *Salmonella paratyphi A* and *B*, *S. typhi*, *S. enteritidis*, *S. cholerae suis* and *S. typhimurium* (S.=Salmonella, and Shigella bacteria, for example *Shigella dysenteriae, Sh. ambigua, Sh. flexneri, Sh. boydii* and *Sh. sonnei* (Sh.=Shigella);

Pseudomonadaceae, such as Pseudomonas bacteria, for example *Pseudomonas aeruginosa* and *Ps. pseudomallei* (Ps.=Pseudomonas), and Aeromonas bacteria, for example *Aeromonas liquefaciens* and *A. hydrophila* (A.-=Aeromonas);

Parvobacteriaceae, such as Pasteurella bacteria, for example *Pasteurella multocida, Past. pestis* (Yersinia) and *Past. pseudotuberculosis* (Past=Pasteurella), Haemophilus bacteria, for example *Haemophilus influenzae, H. ducreyi, H. suis, H. canis* and *H. aegypiteus* (H.=Haemophilus) and Bordetella bacteria, for example *B. bronchiseptica* (B.=Bordetella);

Bacteroidaceae, such as Bacteroides bacteria, for example *Bacteroides fragilis* and *B. serpens* (B.=Bacteroides), Fusiforme bacteria, for example *Fusobacterium fusiforme*, and Sphaerophorus bacteria, for example *Sphaerophorus necrophorus, Sph. necroticus* and *Sph. pyrogenes* (Sph.=Sphaerophorus);

Bacillaceae, such as aerobic spore-forming Bacillaceae, for example *Bacillus anthracis, B. subtilis* and *B. cereus* (B.=Bacillus), anaerobic spore-forming Chlostridia, for example *Clostridium perfringens, Cl. septicium, Cl. oedematien, Cl. histolyticum, Cl. tetani* and *Cl. botulinum* (Cl.=Clostridium).

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis; and local infections.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:

(a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain coloring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following tablets, (including lozenges and granulates) pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 1 to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the abovementioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously intravenously), rectally or locally, preferably orally or parentally. Preferred pharmaceutical compositions and medicaments are therefore those adapted for oral or parenteral administration. Administration in the method of the invention is preferably intravenously or intramuscularly.

In general, it has proved advantageous both in human medicine and in veterinary medicine to administer the active compound or compounds according to the invention in total amounts of 5 to 1,000, preferably 20 to 200, mg/kg of body weight every 24 hours, optionally in the form of several individual administrations, in order to achieve the desired results. An individual administration preferably contains the active compound or compounds according to the invention in amounts of 1 to 250, especially 10 to 100, mg/kg of body weight. However, it can be necessary to deviate from the dosages mentioned, and in particular to do so as a function of the nature and the body weight of the subject to be treated, the nature and the severity of the illness, the nature of the formulation and of the administration of the medicament, and the time or interval over which the administration takes place. Thus it can suffice in some cases to manage with less than the abovementioned amount of active compound, while in other cases the above-mentioned amount of active compound must be exceeded. The particular optimum dosage required and the type of administration of the active compounds can be easily determined by anyone skilled in the art, on the basis of his expert knowledge.

When used as feedstuff additives, the new compounds can be administered in the customary concentrations and formulations, together with the feedstuff or with feedstuff formulations or with the drinking water. By this means it is possible to prevent, alleviate and/or cure an infection by Gram-negative or Gram-positive bacteria and also to achieve promotion of growth and better utilization of the feedstuff.

The new penicillins and cephalosporins are distinguished by powerful antibacterial actions, which have been tested in vivo and in vitro.

For the purpose of broadening the spectrum of action and in order to achieve a more powerful action, especially in the case of $\beta$-lactamese-forming bacteria, the penicillins and cephalosporins according to the invention can be combined with other antimicrobial active compounds, for example with penicillins which are particularly penicillinase-resistant. Such a combination would be, for example, that with oxacillin or dicloxacillin.

For the purpose of broadening the spectrum of action and in order to achieve a more powerful action, the penicillins and cephalosporins according to the invention can also be combined with aminoglycoside antibiotics, such as, for example, gentamycin, kanamycin, sisomycin, amikacin or tobramycin.

The activity of the $\beta$-lactam antibiotics according to the invention can be demonstrated, by way of example, by the following in vitro experiments:

1. In vitro experiments

The compounds of Examples 1(d) and 2, which can be regarded as typical representatives of the compounds according to the invention, were diluted to a content of 100 $\mu$g/ml with Muller-Hinton nutrient broth, 0.1% of glucose being added. In each case, the nutrient solution contained $1\times10^5$ to $2\times10^5$ bacteria per milliliter. The small tubes containing this batch were in each case incubated for 24 hours and the degree of turbidity was then determined. Freedom from turbidity indicates action. At a dosage of 100 $\mu$g/ml, the following bacterial cultures were free from turbidity (sp.=species): *Klebsiella pneumoniae; Enterobacter aerogenes sp.; Providencia; Serratia marcescens; E. coli BE;* Salmonella sp.; Shigella sp.; Proteus, indole-negative and indole-positive; *Pasteurella pseudotuberculosis;* Brucella sp.; *Haemophilus influenzae; Bordetella bronchiseptica; Staphylococcus aureus* 133; *Neisseria catarrhalis sp.; Diplococcus pneumoniae sp.; Streptococcus pyogenes W.; Enterococcus sp.;*

*Lactobacillus sp.; Corynebacterium diphteriae gravis; Corynebacterium pyogenes M; Clostridium tetani;* and *Pseudomonas aeruginosa sp.*

The synthesis of the novel compounds is shown in the following examples, the products being characterized by their NMR spectra wherein the symbols have the following meanings:

| | |
|---|---|
| a | = singlet |
| d | = doublet |
| q | = quartet |
| m | = multiplet |
| AB | = AB system |

Explanation of the abbreviations used in the examples:

| | |
|---|---|
| vol. | = volume |
| pts. by wt. | = parts by weight |
| pts. by vol. | = parts by volume |
| hrs. | = hours |
| hr. | = hour |
| THF | = tetrahydrofuran |
| ether | = diethyl ether |
| ethyl acetate | = acetic acid ethyl ester |
| ° | = °C. |
| room temperature | = about 20° C. |
| abs. | = absolute |
| dcomp. pt. | = decomposition point |

The data in % for the yield denote yields in % of theory.

EXAMPLE 1

(a) Preparation of 2-t-Butoxycarbonylamino-furfurylacetic acid

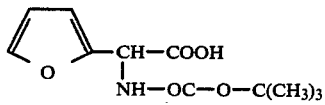

5.0 pts. by wt. of 2-amino-furfurylacetic acid (Röhm and Haas, Netherlands Application No. 66,07754) in 100 pts. by vol. of 80 percent strength aqueous dioxane are brought to pH with 4 N sodium hydroxide solution. 8.0 pts. by wt. of 2-(t-butoxycarbonyloxyimino)-2-phenylacetonitrile are added and the mixture is warmed to 70° for 2 hrs. During this time, the above pH is maintained by adding 4 N sodium hydroxide solution. Thereafter, 80 pts. by vol. of water are added, the dioxane is stripped off and the reaction mixture is extracted several times with ethyl acetate. The aqueous phase is brought to pH 4 with 10 percent strength citric acid, and is saturated with sodium chloride and extracted by shaking with ethyl acetate. The ethyl acetate phases are dried over sodium sulphate and concentrated. The residue is recrystallized from a little abs. carbon tetrachloride. 4.3 pts. by wt. of 2-t-butoxycarbonylamino-furfurylacetic acid of melting point 99°–101° are obtained.

IR(KBr): 3,357, 1,720, 1,686, 1,513, 1,154 and 747 cm$^{-1}$.

NMR(CD$_3$OD): pseudo-s 7.42(1H), pseudo-s 6.35(2H), a 5.30(1H) and s 1.45(9H)ppm (δ).

(b) Preparation of 7-[α-(t-Butoxycarbonylamino)-furfuryl-acetamido]-3-acetoxymethyl-ceph-3-em-4-carboxylic acid

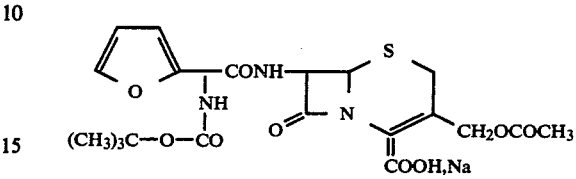

1.7 pts. by wt. of triethylamine and 0.1 pt. by wt. of N-methylmorpholine are added to a solution of 3.7 pts. by wt. of 2-t-butoxycarbonylamino-furfurylacetic acid in 60 pts. by vol. of abs. THF. The mixture is cooled to −25°, a solution of 1.8 pts. by wt. of chloroformic acid ethyl ester in 10 pts. by vol. of abs. THF is added and the mixture is stirred at this temperature for 15 minutes. A solution, pre-cooled to −20°, of silylated 7-aminocephalosporanic acid (7-ACS) in 40 pts. by vol. of abs. THF (prepared from 5.0 pts. by wt. of 7-ACS and 5.6 pts. by wt. of bis-trimethylsilylacetamide) is then added and the mixture is stirred for 10 minutes at −20° and allowed to come to room temperature. 80 pts. by vol. of ice-water are added, the mixture is adjusted to pH 7.3 and the THF is stripped off. The aqueous phase is extracted with ethyl acetate and is acidified at 0°–5° and again extracted with ethyl acetate. The latter ethyl acetate extracts are dried over magnesium sulphate and concentrated. The product (7.5 pts. by wt.) is obtained as a yellow foam, which can be further processed directly.

(c) Preparation of trifluoroacetate of 7-[α-amino)-furfurylacetamido]-3-acetoxymethyl-ceph-3-em-4-carboxylic acid

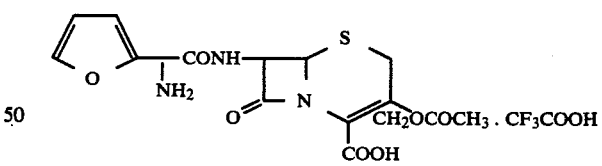

7.5 pts. by wt. of 7-[α-(t-butoxycarbonylamino)-furfurylacetamido]-3-acetoxymethyl-ceph-3-em-4-carboxylic acid are dissolved in 30 pts. by vol. of ice-cold trifluoroacetic acid and the solution is stirred at 0° for 15 minutes. It is poured into a mixture of 120 pts. by vol. of petroleum ether and 60 pts. by vol. of ether, whereupon the product precipitates as the trifluoroacetate. It is filtered off, washed with ether and dried over phosphorous pentoxide and potassium hydroxide. 5.8 pts. by wt. of dcomp. pt. 115°–123°.

(d) Preparation of Sodium 7-{α-[2-oxo-3-furfurylideneamino-imidazolidin-1-yl)-carbonylamino]-furfurylacetamido}-3-acetoxymethyl-ceph-3-em-4-carboxylate

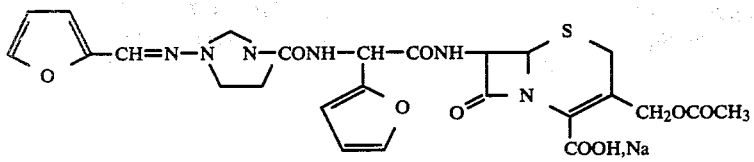

A solution of 5.8 pts. by wt. of 7-[(α-amino)-furfurylacetamido]-3-acetoxymethyl-ceph-3-em-4-carboxylic acid, as the trifluoroacetate, in 100 pts. by vol. of 80 percent strength aqueous THF is cooled to 5° and brought to pH 8 with 1 N sodium hydroxide solution. 2.8 pts. by wt. of 1-chlorocarbonyl-2-oxo-3-furfurylideneamino-imidazole are added in portions, during which the pH is kept at 7.5 with 0.5 N sodium hydroxide solution. When the pH value is constant, 100 pts. by vol. of water are added and the THF is stripped off. The aqueous solution is extracted with ethyl acetate, cooled to 5°, covered with a layer of 150 pts. by vol. of ethyl acetate and acidified with 1 N hydrochloric acid, whereupon the product acid precipitates (3.5 pts. by wt.). It is suspended in 35 pts. by vol. of water and dissolved with 0.5 N sodium hydroxide solution, and the solution obtained is lyophilized. 3.0 pts. by wt. of the sodium salt of dcomp. pt. 170°–180° are obtained.

IR (KBr): 3,420, 1,765, 1,725, 1,675, 1,605, 1,415 and 1,235 cm$^{-1}$.

NMR (CD$_3$OD): s 7.75(1H), pseudo-s 7.64(1H), pseudo-s 7.50(1H), d 6.89(1H), m at 6.5(3H), m at 5.65(2H), m at 5.0 (partially overlaid by the signal of the replaceable protons), s(broad) 3.93(4H), AB at 3.4 and 3.6 (overlaid by the solvent signal) and s 2.02(3H) ppm (δ).

| $C_{25}H_{23}N_6N\ O_{10}S \cdot 2.5\ H_2O$ | | | |
|---|---|---|---|
| calculated: | C 44.95 | H 4.23 | N 12.59 | S 4.80 |
| found: | C 44.9 | H 4.1 | N 12.8 | S 4.8 |

EXAMPLE 2

Preparation of Sodium 6-{α-[(2-oxo-3-furfurylideneamino-imidazolidin-1-yl)-carbonylamino]-furfurylacetamido}-penicillanate

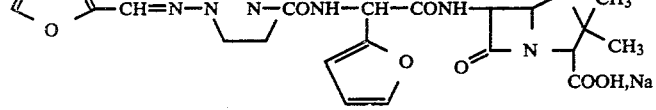

2.4 pts. by wt. of α-amino-furfurylacetamido-penicillanic acid (Beecham, U.S. Pat. No. 3,120,514) and 2.4 pts. by wt. of 1-chlorocarbonyl-2-oxo-3-furfurylideneamino-imidazole are reacted and worked up as in Example 1(d). 1.3 pts. by wt. of dcomp. pt. 180°–185° are obtained, with a β-lactam content of 82%.

IR(KBr): 1,760, 1,715, 1,660 and 1,605 cm$^{-1}$.

NMR(CD$_3$OD): s 7.72(1H), d 7.70(1H), pseudo-s 7.50(1H), d 6.85(1H), m at 6.60(3H), s 5.55(1H), AB 5.38 and 5.42(2H), s 4.12(1H), s(broad) 3.80(4H), s 1.53(3H) and s 1.48(3H) ppm (δ).

EXAMPLE 3

Preparation of Sodium 6-{α-[(2-oxo-3-furfurylideneamino-imidazolidin-1-yl)-carbonylamino]-thiazolyl-4-acetamido}-penicillanate

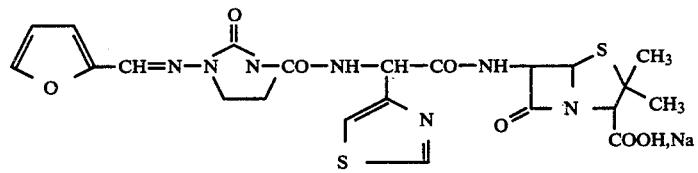

4.3 parts by wt. of α-amino-thiazolyl-4-acetamidopenicillanic acid (crude product; M. Hatanaka and T. Ishimaru, J. Medicinal Chemistry 1973, 16 pages 978–84) are dissolved in 120 pts. by vol. of 80% strength aqueous tetrahydrofuran and the pH of the mixture is adjusted to 7.5 by adding an appropriate amount of triethylamine. 3.3 pts. by wt. of 1-chlorocarbonyl-2-oxo-3-furfurylidene-amino-imidazole are introduced and the pH is kept at 7.5 by adding triethylamine. If the pH remains constant by itself, the mixture is diluted with 100 parts by vol. of water, and is extracted by shaking twice with ethyl acetate, covered with a layer of fresh ethyl acetate and acidified down to pH 1.5 with 2 N HCl, while stirring. Some of the penicillanic acid liberated precipitates as an oil. The ethyl acetate phase is dried and the penicillin required is precipitated from this by adding a 1 molar solution of sodium 2-ethylhexanoate in methanol-containing ether.

Yield: 1.1 parts by wt.

Dcomp. pt.: 215° C.

β-lactam content 74%

IR (Nujol, carbonyl range): 1,765, 1,715 and 1,665 cm$^{-1}$.

NMR(CD$_3$OD): α8.9 (1H, thiazole), s 7.7 (1H) and s (2H) (furan, thiazole and —CN=N—), m 6.85 (1H, furan), m 6.5 (1H, furan) m 5.6–5.35 (3H), m 3.8 (4H) 1.70–145 (6H) ppm (δ).

EXAMPLE 4

Preparation of Sodium 6-{α-[(2-oxo-3-furfurylideneamino-imidazolidin-1-yl)-carbonylamino]-thienyl-2-acetamido}-penicillanate

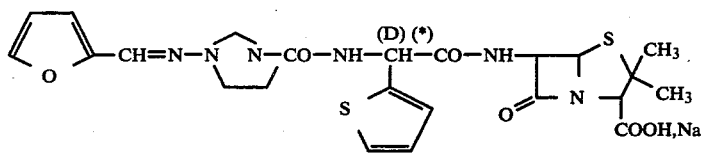

*)Because of the NMR spectrum and the good activity, it must be assumed that the D form is present. Since the racemate of the α-amino-thienylacetic acid was used as the starting material, a diastereomer separation must have occured at the stage of the α-amino-thienylmethyl-penicillin.

0.6 part by wt. of α-amino-thienyl-2-acetamido-penicillanic acid (M. Hatanaka and T. Ishimaru, J. Medicinal Chemistry 1973, 16, pages 978–84) are dissolved at pH 7.5–8.0 in 40 pts. by vol. of 80% strength aqueous tetrahydrofuran by adding only just the required amount of triethylamine. The acid is then reacted with 0.42 pt. by wt. of 1-chlorocarbonyl-2-oxo-3-furfurylideneamino-imidazole in the manner described in Example 1(d), and the mixture is worked up.

Yield: 0.7 pt. by wt.

β-lactam content: 85% (substance contains 6% of a product with an open β-lactam ring).

IR (Nujol; carbonyl range): 1,760 (shoulder), 1,750, 1,715, 1,655, 1,595 and 1,520-10 cm$^{-1}$.

NMR (CD$_3$OD/D$_2$O): 7.7–6.9 m (5H, thiophene, furan, —CH=N—), 6.8 d (1H, furan), 6.5 m (1H, furan), 5.8 s (1H,

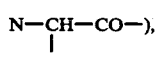

5.5 pseudo-s (2H, 5.6-H), 4.2 s (1H, 3-H), 3.9–3.6 s, broad (4H,

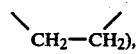

1.55 s (3H) and 1.45 s (3H) ppm (δ).

According to the NMR spectrum, the substance contains 0.08 molar equivalent of sodium 2-ethylhexanoate and 3.2 molar equivalents of water.

EXAMPLE 5

Preparation of Sodium 6-{α-[(2-oxo-3-furfurylideneamino-imidazolidin-1-yl)-carbonylamino]-(5-methyl-isoxazol-3-yl)-acetamido}-penicillanate

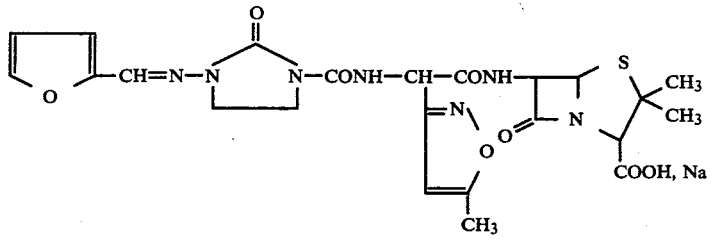

The preparation is carried out analogously to Example 2; dcomp. pt. 205°–210°.

IR (KBr): 1,770, 1,725, 1,675, 1,605, 1,525, 1,475, 1,410, 1,270 and 1,235 cm$^{-1}$.

NMR (CD$_3$OD): s. 7.71 (1H), d 7.62 (1H), d 6.89 (1H), dd 6.54 (1H), broad s 6.22 (1H), m between 5.7 and 5.3 (3H), s 4.22 (1H), s 3.90 (4H), s 2.37 (2H), s 1.62 (3H) and s 1.56 (3H) ppm (δ).

EXAMPLE 6

(a) Preparation of 2-(1,3,5-Trimethylpyrazol-4-yl)-2-aminoacetic acid

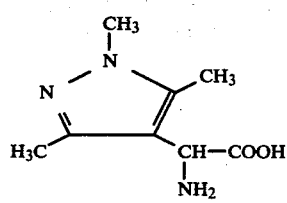

A mixture of 13.8 pts. by wt. of 1,3,5-trimethyl-pyrazole-4-aldehyde, 5 pts. by wt. of sodium cyanide, 5.9 pts. by wt. of ammonium chloride, 13.4 pts. by vol. of concentrated ammonia solution, 30 pts. by vol. of water and 30 pts. by vol. of ethanol is left to stand at 60° for 5 hrs. in a closed flask, with occasional swirling.

The reaction solution is then added to 80 pts. by vol. of ice-cold concentrated hydrochloric acid and rinsed with water, and 50–60 g of HCl gas is passed, at 0°–5°, into the solution, which is then left to stand overnight (fume cupboard). After diluting the mixture with 100 pts. by vol. of water, boiling it under reflux for 2.5 hrs. and concentrating it, the residue is evaporated, with fuming, twice with water in a porcelain dish (in order to remove HCl).

Finally, the residue is taken up in ethanol, the insoluble material is filtered off, the filtrate is concentrated to dryness, the residue is taken up again in water and the mixture is stirred with about 50 g of an acid ion exchanger (Dowex from Messrs. Serva, Heidelberg) (5 hours).

The laden ion exchanger is then filtered off, rinsed thoroughly with water and finally eluted with ammonium carbonate solution. The solution obtained is concentrated to dryness. The residue is washed with ethanol and 7.4 pts. by wt. (40%) of the desired aminoacid are obtained from the mother liquors.

60 MHz-NMR spectrum (D₂O): 2.05 ppm s (3H), 2.15 s (3H), 3.6 s (3H), 4.8 (water) and 4.9 s (1H). A single compound according to thin layer chromatography, R$_f$=0. (Running agent: 200 ml of n-butyl acetate, 36 ml of n-butanol and 100 ml of acetic acid (treated with 150 ml of phosphate buffer pH 6)).

(b) Preparation of 2-(1,3,5-Trimethylpyrazol-4-yl)-2-tert.-butoxycarbonylamino-acetic acid

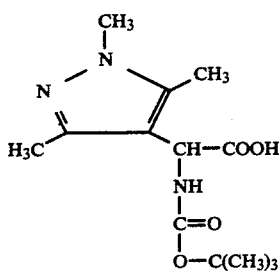

20.3 pts. by wt. of di-t-butyl carbonate are slowly added to a mixture of 16.1 pts. by wt. of the aminoacid from Example 6(a)., 3.52 pts. by wt. of sodium hydroxide, 18 pts. by vol. of t-butanol and 9 pts. by vol. of water at 0°, a further 18 pts. by vol. of t-butanol are added and the mixture is subsequently stirred at 25° for 14 hours and then at 50° for 12 hours. It is diluted with 50 pts. by vol. of water, washed 3 times in each case with n-pentane and ether and acidified to pH 2.4. After extracting the mixture with acetic acid ethyl ester (4 ml) and drying the extract over Na₂SO₄ and concentrating it, the residue is dried under a high vacuum.

60 MHz-NMR spectrum (CDCl₃): 1.4 ppm s (9H), 2,4 s (3H), 2.45 s (3H), 3.7 s (3H), 5.1 d (1H), 5.8 d (1H) and 12.6 s (1H).

Yield: 15 pts. by wt. (63%) of 2-(1,3,5-trimethyl-pyrazol-4-yl)-2-tert.-butoxycarbonylaminoacetic acid.

(c) Preparation of 7-[2-1,3,5-Trimethylpyrazol-4-yl)-2-t-butoxycarbonylamino-acetamido]-cephalosporanic acid

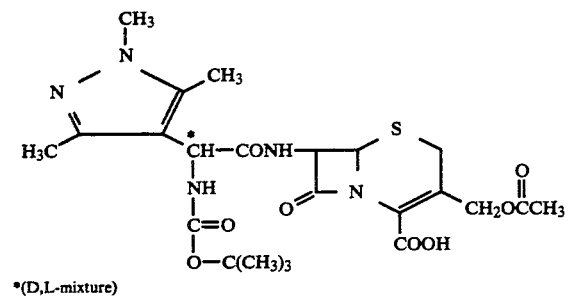

*(D,L-mixture)

5.36 pts. by wt. of the compound from Example 6(b) are dissolved in 150 pts. by vol. of tetrahydrofuran and 2 pts. by wt. of triethylamine, 2.75 pts. by wt. of chloroformic acid iso-butyl ester are added at −15° and the mixture is subsequently stirred at −10° for 1.5 hrs. (Solution A).

Solution B:

5.44 pts. by wt. of 7-aminocephalosporanic acid are dissolved in 100 pts. by vol. of 80% strength aqueous tetrahydrofuran and 2 pts. by wt. of triethylamine and the solution is cooled to −10°. Solution A is added dropwise to this solution at −10°. The mixture is subsequently stirred at −10° for 1.5 hrs. and then for a further 2 hrs., it being allowed to come to room temperature.

The reaction solution is added to 100 pts. by vol. of water, washed with ethyl acetate, acidified (pH 1.8) and extracted with ethyl acetate and this ethyl acetate solution is washed with saturated NaCl solution. After drying over MgSO₄, the ethyl acetate solution is concentrated and the residue is dried under a high vacuum.

Yield: 7.5 pts. by wt. (70%) of the compound described above.

A single compound according to the thin layer chromatogram, R$_f$ value 0.3 (running agent mixture as in Example 6 (a))

100 MHz-NMR spectrum (CDCl₃): 1.4 ppm s (9H), 2.1 s (3H) 2.3 m (6H), 3.4 AB (2H), 3.7 m (3H), 4.95 AB (2H), 5.05 d (1H) (I=3Hz), 5.3 d (1H) (I=3Hz), 5.8 d (1H), 7.3 d (1H) and 10.8 s (1H).

(d) Preparation of 7-[2-(1,3,5-Trimethylpyrazol-4-yl)-2-amino]-acetamido-cephalosporanic acid

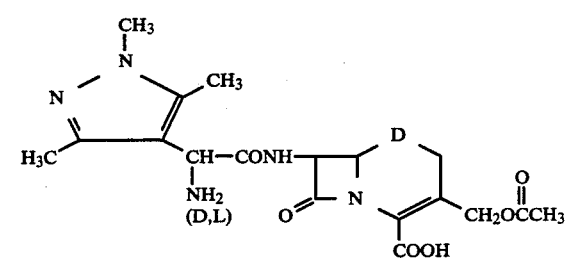

12.3 pts. by vol. of trifluoroacetic acid and 1.4 pts. by vol. of anisole are cooled to 0° and 4 pts. by wt. of the compound from Example 6(c) are added, while stirring.

The trifluoroacetic acid is then essentially distilled off (receiver cooled to −70°, high vacuum), the residue is dissolved in 10 pts. by vol. of methylene chloride and the solution is stirred for 20 minutes. 100 pts. by vol. of ether/ligroin 1:1 are then added, the mixture is subsequently stirred for a further 30 minutes and the precipitate is filtered off and taken up in water.

After covering the aqueous solution with a layer of ethyl acetate/ether, the mixture is adjusted to pH 7 with Amberlite (liquid ion exchanger, chloride as the ion of opposite charge), the phases are separated and the aqueous phase is washed very throughly with ether. The aqueous phase is freeze-dried.

Yield: 3 pts. by wt. of 7-[2-(1,3,5-trimethylpyrazol-4-yl)-2-amino]-acetamidocephalosporanic acid.

Thin layer chromatogram (for the running agent see Example 6(a)): a spot at the starting point.

IR (KBr) 3,422, 2,923, 1,763, 1,689, 1,599, 1,383, 1,235, 1,064, 1,026 and 730.

100 MHz-NMR spectrum (D₂O): 2.1 ppm 2 s (separation 0.5 Hz) 3H (ratio 1:1), 2.2 m (3H) 2.3 m (3H), 3.4 and 3.6 AB (2H), 3.7 s (3H), 4.7 s (4 replaceable H+1×H₂O), 5.15 m (3H) and 5.7 m (1H).

(e) Preparation of Sodium 7-{2-(1,3,5-trimethylpyrazol-4-yl)-2-[(2-oxo-3-furfurylideneaminoimidazolidin-1-yl)-carbonylamino]-acetamido}-cephalosporanate

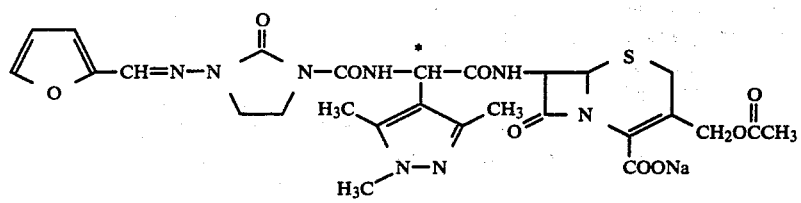

*(D,L mixture)

1 pt. by wt. of the cephalosporin described in Example 6(d) is dissolved in 80 pts. by vol. of 80% strength aqueous tetrahydrofuran, and 0.53 pt. by wt. of 1-chlorocarbonyl-2-oxo-3-furfurylideneamino-imidazole is added the mixture being kept at pH 7-8 with NaOH; temperature 5°.

The working up is as described in Example 1(d).

Yield: 1.2 pts. by wt. (78%) of the compound described above.

IR spectrum (Nujol): β-lactam band at 1,765.

Thin layer chromatogram (running agent as for Example 6(a)). $R_f$ value: 0.2 (single compound).

100 MHz-NMR spectrum (CD$_3$OD+D$_2$O): 2.15 ppm s (3H), 2.3 m (3H), 2.45 m (3H), 3.4 AB (overlaid by the solvent signal and following signals) (2H), 3.8 s (3H), 4.0 s (broad) (4H), 4.9–5.2 m (partially overlaid by replaceable hydrogens) (4H), 5.5 d (J=O, 5Hz) (1H), 7.0 d (1H), 7.8 d (1H), and 7.85 s (1H).

EXAMPLE 7

Preparation of Sodium 6α-methoxy-6β-{D-2-[(2-oxo-3-furfurylideneamino-imidazolidin-1-yl)-carbonylamino]-thienyl-2-acetamido}-penicillinate

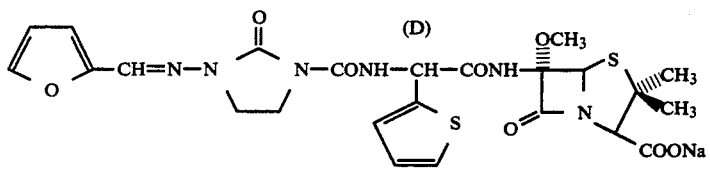

0.067 pt. by wt. of lithium hydride in 20 ml of methanol is added to 1.9 pts. by wt. of 6-{D-2-[(2-oxo-3-furfurylideneamino-imidazolidin-1-yl)-carbonylamino]-thienyl-2-acetamido}-penicillanic acid in 40 pts. by vol. of absolute tetrahydrofuran at −80°; 0.4 pt. by wt. of t-butyl hypochlorite is then added and the mixture is subsequently stirred at −60° for 2 hours.

The reaction solution is then added to a 10% strength ammonium chloride solution and the pH value is kept at 7 with further addition of dilute hydrochloric acid. The tetrahydrofuran is distilled off in vacuo and the aqueous phase is washed with ethyl acetate. 10 pts. by vol. of acetone are then added and the pH value is slowly adjusted to 4 with dilute hydrochloric acid, while stirring. The penicillanic acid slowly crystallizes out. The precipitate is filtered off and dissolved in water at a pH value of 7, 1 N sodium hydroxide solution being added. Finally the solution is lyophilized.

1.8 pts. by wt. (86%) of the compound described above are obtained.

Thin layer chromatogram: $R_f$ value 0.6, single compound. IR spectrum (KBr): 3,436, 1,762, 1,726, 1,674, 1,604, 1,529, 1,476, 1,413, 1,270, 1,235, 1,136 and 740.

100 MHz-NMR spectrum (CD$_3$OD): 1.3 ppm s (3H), 1.5 s (3H), 3.6 s (3H), 4.0 s (broad) (4H), 4.3 s (1H), 5.65 s (1H), 6.0 d (1H), 6.65 q (1H), 7.0 d (1H), 7.1–7.5 m (5H), 7.75 d (1H) and 7.8 s (1H).

The following table indicates minimum inhibitory concentration values on the specified germs by the mentioned compounds of the present invention.

| | MINIMUM INHIBITORY CONCENTRATION values Compounds | | | |
|---|---|---|---|---|
| Germs | Example 4 | Example 6(e) | 1:1 mixture of Example 4 + Example 6(e) | 2:1 mixture of Example 4 + Example 6(e) |
| E.coli T 7 | 128–256 | 1 | 4 | 4–16 |
| E.coli A 261 | 32–64 | 1 | 4 | 4–16 |
| E.coli Neumann | 0.25 | 1 | ≦0.25 | ≦0.25 |
| E.coli 183/58 | 0.5–1 | 8–16 | 1 | 1 |
| E.coli F 14 | 256 | 8–16 | 16 | 64 |
| E.coli C 165 | 0.25 | 4 | 1 | 1 |
| E.coli 4 322 | 1 | 4 | 4 | 1 |
| Klebsiella 57 USA | 16 | 1 | 4 | 4–16 |
| Klebsiella 63 | 0.5–1 | 2–4 | 1 | 0.5–1 |
| Klebsiella 1852 | 128–256 | 4 | 16 | 4–16 |
| Klebsiella 6097 | 1 | 4 | 4 | 1 |
| Serratia 16001 | 0.5–1 | 4 | 2–4 | 1 |
| Serratia 16002 | 2–4 | 16 | 4 | 4–16 |
| Providencia 12012 | 1 | 4 | 16 | 1 |
| Prot.morg. 932 | 8–16 | 64 | 16 | 4–16 |
| Prot.morg. 11006 | 1 | 16 | 4 | 1 |
| Prot.vulg. 9023 | 1 | 8–16 | 4 | 1 |
| Prot.vulg. 1017 | 4 | 64 | 16 | 4–16 |
| Prot.rettg. 10007 | 1 | 16 | 4 | 1 |
| Staph.aur. 1756 | 128–256 | 256 | 128–256 | 256 |
| Staph.aur. 133 | 1 | 16 | 4 | 1 |
| Strept. faec. 27101 | 16 | 256 | 64 | 4–16 |
| Enteroc.ATCC 97900 | 32–64 | 256 | 128–256 | 64 |
| Psdm.aerug. F 41 | 16 | 256 | 64 | 4–16 |
| Psdm.aerug. Walter | 16 | 256 | 32 | 4–16 |

The compounds of the present invention, as defined herein also include their pharmaceutically acceptable bioprecursors.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

EXAMPLE 8

(a) Preparation of 2-(2-tert.-butoxy-carbonyl-imino-4-thiazolin-4-yl)-2-methoxy-imino-acetic-acid-ethyl-ester (syn-form):

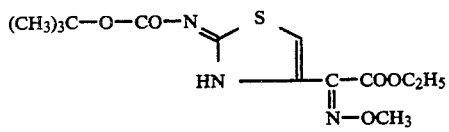

65 gr. of di-tert.-butyl pyrocarbonate are added dropwise to a stirred mixture of 50 gr of 2-(2-amino-thiazol-4-yl)-2-methoxy-imino-acetic-acid-ethyl-ester(syn-form) and 150 ml of tert.-butanol which is warmed to 40°–45° C. The mixture is stirred for further 30 minutes at 40° C. and the solvent is removed in vacuo. The product is dissolved in ether, the solution is washed with hydrochloric acid whereby 13 gr of unreacted starting material precipitates. This material is filtered off, the filtrate is treated with some petrol ether and further 4.5 gr starting material precipitate. The filtrate of this precipitation is evaporated in vacuo, the residue is dissolved in a mixture of petrol ether and acetone (9:1) and chromatographed over a silica gel column. The desired compound is eluted as the second substance and melts at 122°–124° C.

NMR (60 MHz; 67 in CCl₄) 7,05 (s; Thiazolin 5-H).

(b) Preparation of 2-(2-tert.-butoxy-carbonyl-imino-4-thiazolin-4-yl)-2-amino-acetic-acid-ethyl-ester-hydrochloride)

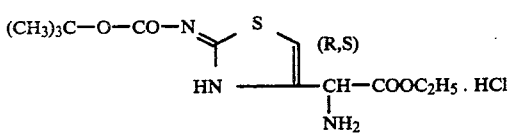

5.6 gr of zinc dust are added to a mixture of 7.0 gr of a compound prepared according to Example 8 (a) and 30 ml of 90% strength aqueous acetic acid which is cooled with ice. The mixture is stirred for 40 minutes at 0° C., then the unreacted zinc dust is filtered off and washed with 50% strength aqueous acetic acid. The filtrate is evaporated in vacuo. The residue is suspended in water of pH 8, H₂S is fed into the mixture, the solid is filtered off and the filtrate is extracted at pH 10 with ethyl acetate. The ethyl acetate solution is extracted with water of pH 3 and this aqueous solution is freeze-dried.

Yield: 4.15 g. IR(Nujol; Carboxyl range) 1730; 1710; 1540 cm⁻¹.

Melting point: Starting at 130° C. with decomposition (c) Preparation of 2-(2-tert.-butoxy-carbonyl-imino-4-thiazolin-4yl)-2-amino-acetic-acid

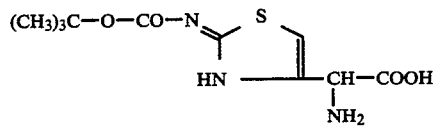

A solution of 4.15 g of the compound obtained according to example 8 (b) in 80 ml 50% strength aqueous ethanol is treated with sodium hydroxide up to pH 13 and the pH is kept for 15–20 minutes. Then the pH is changed to 7.5 with hydrochloric acid and the solution is evaporated in vacuo. The residue consists of the desired compound contaminated with some NaCl.

IR(Nujol; carbonyl range) 1715; 1600; 1545 cm⁻¹.

(d) Preparation of 2-(2-tert.-butoxy-carbonyl-imino-4-thiazolin-4-yl)-2-[(2-oxo-3-furylidine-amino-imidazoline-1-yl)carbonyl-amino]-acetic-acid

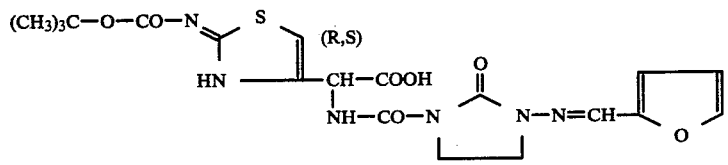

5.0 g of the compound obtained according to example 8(c) containing 2.0 g NaCl are suspended in 70 ml 60% strength aqueous tetrahydrofuran and the mixture is brought to pH 7.5 by means of 2 n NaOH. Then 2.72 g of 1-chloro-carbonyl-2-oxo-3-furylidene-amino-imidazolidine are added and the pH is kept at 7.5 by means of NaOH. When the pH will not change anymore, the tetrahydrofuran is removed in vacuo. The residue is treated with 2 n hydrochloric acid up to pH 2.3, the precipitate is filtered off and washed with water. The precipitate is suspended in hot aqueous ethanol, cooled and filtered off.

Yield: 3.8 g.

Melting point: 226° C.

(e) Preparation of 7-{2-(-tert.-butoxy-carbonyl-imino-4-thiazolin-4-yl)-2-[(2-oxo-3-furylidene-amino-imidazolidine-1-yl)-carbonyl amino]-acetamido}-cephalosporanic acid

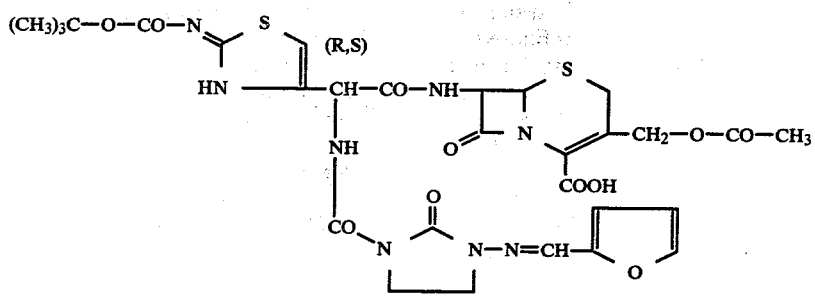

Mixture A:

1.0 g of the compound obtained according to example 8 (d) is treated in 30 ml of dichloromethane with 0,29 ml of triethyl amine. The solution is chilled to −40° C., treated with 0,02 ml of 3-dimethyl-amino-propanol and 0.26 ml of chloroformic acid ethyl ester, stirred for 16 minutes at this temperature, treated with further 0.13 ml chloroformic acid ethyl ester and 0.15 ml of triethyl amine and this is repeated after 30 minutes.

Mixture B:

A suspension of 0.77 g of 7-amino cephalosporanic acid in 20 ml of dichloro methane, cooled to 0° C. is treated with 2.0 ml of triethyl amine and then with 20 ml of acetone which is cooled to −10° C. The mixture is then further cooled to −20° C.

Mixture A and B are combined and stirred. After 2 hours water is added and the pH is brought to 7.5. The mixture is twice extracted with ethyl acetate and the acqueous phase is acidified to pH 2. This solution is 3 x extracted with ethyl acetate. The combined and dried organic phases are evaporated in vacuo and the residue is dried over $P_4O_{10}$.

Yield: 1.05 g.

(f) Preparation of 7-{(2-amino-thiazol-4-yl)-2-[(2-oxo-3-furylideneaminoimidazolidine-1-yl)-carbonyl-amino]acetamido}-cephalosporanic acid

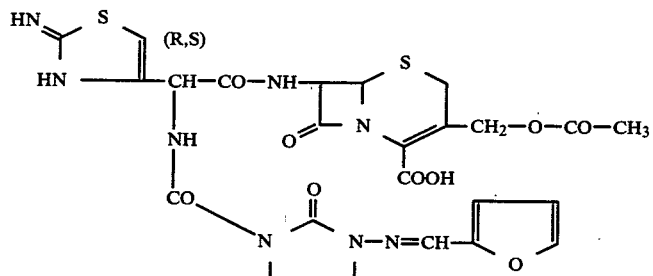

0.7 g of the compound obtained according to example 8(e) are suspended in 2.8 ml of anisole, cooled with ice and water, treated with 14 ml of trifluoro acetic acid and kept for 12 hours at 4° C. The solution is evaporated at −25° C. in vacuo, the residue treated with ether, filtered off and dried over $P_4O_{10}$.

Yield: 0.6 g.

IR-spectrum (carbonyl range) 1740, 1715, 1660 and 1520–1500 cm$^{-1}$ (Nujol).

It will be appreciated that the instant specification and examples are set forth by way of illustration and not limitation, and that various modifications and changes may be made without departing from the spirit and scope of the present invention.

What we claim is:

1. A compound of the formula

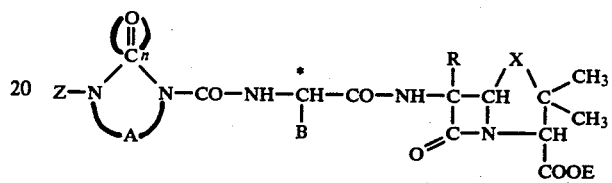

a pharmaceutically usable salt thereof or a hydrate thereof, in which

R is hydrogen or lower alkoxy,

Z is

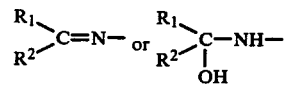

$R_1$ and $R_2$ each independently is hydrogen; alkyl or alkenyl with up to 6 carbon atoms; cycloalkyl, cycloalkenyl or cycloalkadienyl with up to 10 carbon atoms; phenyl—$C_{1-4}$—alkyl; phenyl; naphthyl; phenyl or naphthyl substituted by halogen, $C_1$—$C_4$—alkyl, $C_1$-$C_4$—alkoxy, nitro, cyano, $C_1$-$C_4$—alkylsulphonyl or $CH_3COO$; heterocyclyl selected from the group consisting of thienyl, furyl, oxazolyl, isoxazolyl, thiazolyl, isothiazolyl, pyrrolyl, imidazolyl, pyrazolyl, oxdiazolyl, thiadiazolyl, triazolyl, oxtriazolyl, thiatriazolyl, tetrazolyl, pyridyl, pyrazinyl, pyrimidinyl, tetrahydrofuranyl, dioxanyl, pyrrolidinyl, piperidinyl, morpholinyl, pyron-2-yl and pyron-4-yl, the heterocyclyl being unsubstituted or substituted by lower alkyl, trifluormethyl, halogen, amino, lower alkyl-amino, di-lower alkylamino, formylamino, acetylamino, $CH_3OCONH$, $C_2H_5OCONH$, $CH_3SO_2NH$, hydroxyl, methoxy, ethoxy, methylthio, ethylthio, $CH_3SO_2$, $CH_3SO$, HOOC, $HO_3S$, HCO, lower alkyl-CO, lower alkoxy-CO or CN attached to a carbon atom of the ring, or substituted by lower alkyl, CN, CHO, lower alkyl-COO, NH₂-CO, lower alkyl-NH-CO, lower-alkyl-CO attached to a nitrogen atom of the ring; carboxyl; methoxycarbonyl; ethoxycarbonyl; cyano; nitro; lower alkyl-carbonyl; CONH₂; CONHCH₃; CON(CH₃)₂; SO₂NH₂; SO₂-NHCH₃ or SO₂N(CH₃)₂; or R₁ and R₂ together with the carbon atom to which they are bonded form a ring of the formula

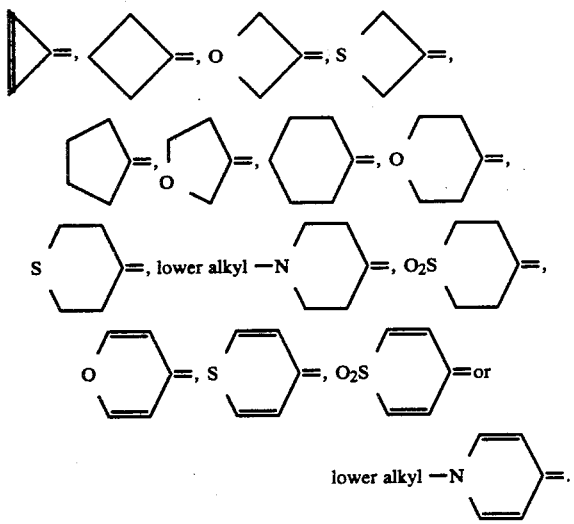

A is —CH₂—CH₂—; —CH₂—CH₂—CH₂— or

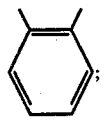

n is 1 or 2;
B is a heterocyclic radical selected from the group consisting of pyrazolyl, imidazolyl, oxazolyl, oxdiazolyl, 2-amino- and 2-oxo-Δ⁴-thiazolinyl, tetrazolyl, sudnonyl, furylthienyl, pyrrolyl, thiazolyl, isothiazolyl, isoxazolyl, and thiadiazolyl, said heterocyclic radical being unsubstituted or substituted by halogen, $C_1$–$C_6$-alkyl, cyano, sulpho or methylsulfonyl;

X is S, O, SO, SO₂ or CH₂; and

E is hydrogen, a pharmaceutically usable salt-forming cation or a conventional protective group.

2. A compound according to claim 1, in which C is in the D=R configuration.

3. A compound according to claim 1, in which E denotes a pivaloyl group.

4. A compound according to claim 2, in which
R is hydrogen or methoxy;
R¹ denotes hydrogen;
R₂ is phenyl; phenyl substituted by halogen, $C_1$—$C_4$—alkyl, $C_1$—$C_4$—alkoxy, nitro, cyano, $C_1$—$C_4$—alkylsulfonyl, or CH₃OOC; furyl; thienyl; furyl or thienyl substituted by halogen, nitro, $C_1$—$C_4$—alkyl, $C_1$—$C_4$—alkoxycarbonyl or CH₃COOCH₂; pyridyl; $C_1$—$C_6$—alkyl; $C_2$—$C_6$—alkenyl; or $C_3$—$C_{10}$—cycloalkyl, -cycloalkenyl or -cycloalkadienyl;
A is —CH₂—CH₂—; and
B is furyl, thienyl, pyrrolyl, imidazolyl, thiazolyl, isothiazolyl, isoxazolyl or thiadiazolyl.

5. A compound or salt according to claim 4, in which R² denotes phenyl substituted by fluorine, chlorine, bromine, methyl, methoxy or methylsulphonyl; furyl or thienyl substituted by chlorine or bromine; pyrid-3-yl; cyclohexyl or alkyl or alkenyl with up to 4 carbon atoms.

6. A compound or salt according to claim 5, in which the alkyl and alkenyl groups mentioned are substituted by halogen or alkoxy with 1 to 4 carbon atoms.

7. A compound or salt according to claim 5, in which R² denotes furyl or thienyl substituted in the 4-position or 5-position and bonded in the 2-position or 3-position, or denotes alkyl or alkenyl substituted by methoxy.

8. The compound according to claim 1, of the formula

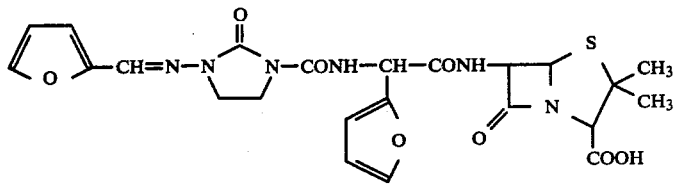

or a pharmaceutically usable salt thereof.

9. The compound according to claim 1, of the formula

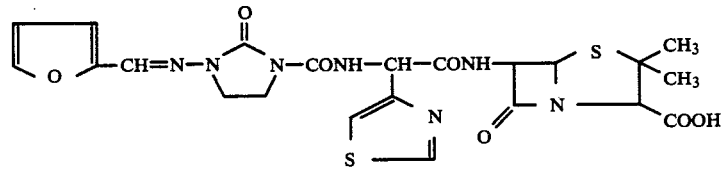

or pharmaceutically usable salt thereof.

10. The compound according to claim 1, of the formula

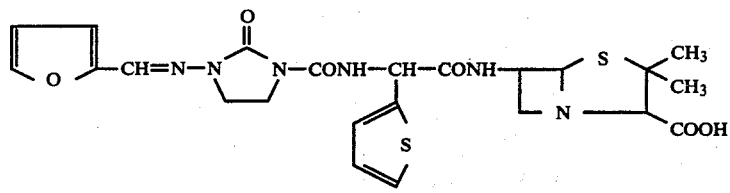

or a pharmaceutically usable salt thereof.

11. The compound according to claim 1, of the formula

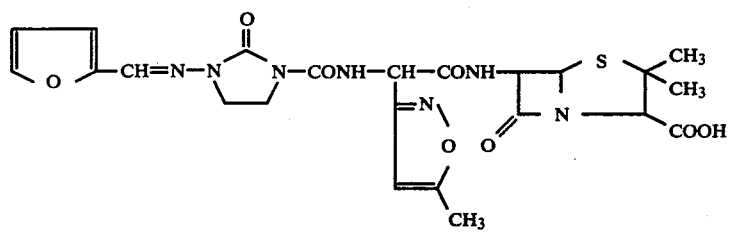

or a pharmaceutically usable salt thereof.

12. The compound according to claim 1, of the formula

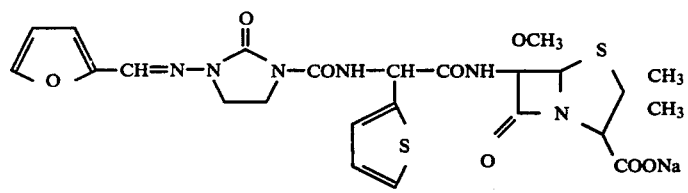

or a pharmaceutically usable salt thereof.

13. A pharmaceutical composition containing as an active ingredient an antibacterially effective amount of a compound according to claim 1 in admixture with a diluent.

14. A medicament in dosage unit form comprising a composition according to claim 13.

15. A method of combating bacterial diseases in human and non-human animals which comprises administering to the animals an antibacterially effective amount of a compound according to claim 1.

16. An animal feedstuff comprising feed and a growth-promoting amount of a compound according to claim 1.

17. A method of promoting growth and improving feedstuff utilization in animals which comprises administering to the animals an effective amount of a compound according to claim 1.

18. A method of preserving organic or inorganic materials which comprises applying to said materials a protective amount of a compound according to claim 1.

* * * * *